United States Patent [19]
Gaeta et al.

[11] Patent Number: 5,863,936
[45] Date of Patent: *Jan. 26, 1999

[54] TELOMERASE INHIBITORS

[75] Inventors: Federico C.A. Gaeta, Foster City; Adam A. Galan, Alameda; Elaine C. Stracker, Vacaville, all of Calif.

[73] Assignee: Geron Corporation, Menlo Park, Calif.

[*] Notice: The term of this patent shall not extend beyond the expiration date of Pat. No. 5,703,116.

[21] Appl. No.: 549,597

[22] Filed: Oct. 27, 1995

Related U.S. Application Data

[63] Continuation-in-part of Ser. No. 424,813, Apr. 18, 1995, Pat. No. 5,703,116, and a continuation-in-part of Ser. No. 425,043, Apr. 18, 1995, Pat. No. 5,760,062.

[51] Int. Cl.$^6$ ...................... C07D 333/64; C07D 333/66; A61K 31/38
[52] U.S. Cl. .............. 514/443; 549/51; 549/52; 549/53; 549/54; 549/55; 549/56; 549/57; 549/58
[58] Field of Search ................ 514/443; 549/51, 549/52, 53, 54, 55, 56, 57, 58

[56] References Cited

U.S. PATENT DOCUMENTS

| | | | |
|---|---|---|---|
| 4,269,846 | 5/1981 | Huang et al. | 424/269 |
| 4,391,627 | 7/1983 | Levitt | 71/90 |
| 4,611,059 | 9/1986 | Sih | 546/274 |
| 4,863,923 | 9/1989 | Ho et al. | 514/443 |
| 5,169,860 | 12/1992 | Mohamadi et al. | 514/415 |
| 5,208,253 | 5/1993 | Boschelli et al. | 514/443 |
| 5,346,907 | 9/1994 | Kerwin, Jr. et al. | 514/312 |
| 5,703,116 | 12/1997 | Gaeta et al. | 514/443 |

FOREIGN PATENT DOCUMENTS

| | | | |
|---|---|---|---|
| 0 050957 A1 | 5/1982 | European Pat. Off. | 409/6 |
| 0 069521 A2 | 1/1983 | European Pat. Off. | 405/6 |
| 0 158380 B1 | 10/1985 | European Pat. Off. | 333/70 |
| 0 483647 A1 | 10/1990 | European Pat. Off. | 333/68 |
| 0 512349 A1 | 11/1992 | European Pat. Off. | 333/70 |
| 0 568289 A2 | 11/1993 | European Pat. Off. | 333/70 |
| 0 572712 A2 | 12/1993 | European Pat. Off. | 333/56 |
| 0 619297 A1 | 10/1994 | European Pat. Off. | 237/48 |
| 729964 | 4/1996 | European Pat. Off. | |
| 1936721 | 5/1969 | Germany. | |
| 1927393 | 12/1969 | Germany. | |
| 92/03427 | 3/1992 | Japan. | |
| 93/02037 | 2/1993 | WIPO | 53/6 |
| 93/23572 | 11/1993 | WIPO | 1/68 |
| WO 95/10513 | 4/1995 | WIPO. | |

OTHER PUBLICATIONS

STN search results for: Jagodzinski, A Friedel–Crafts Synthesis of Secondary Thiophene—and Benzo[b]thiophenecarbothioamides, Pol. J. Chem., vol. 66, No. 4, pp. 653–659, 1992.

STN search results for: Hiremath et al., Synthesis of Substituted 2,5–bis(oxadiazolyl/thiazolidino/pyrazolyl/pyrimidinediono/indoles and Oxadiazolyl/thiadiazolyl/triazolyl/thiazolidinone Analogs of Benzothiophene and Their Antibacterial Activity, Indian, 1992.

(List continued on next page.)

*Primary Examiner*—Mukund J. Shah
*Assistant Examiner*—Deepak R. Rao
*Attorney, Agent, or Firm*—David P. Lentini; Kevin R. Kaster

[57] ABSTRACT

Methods and compositions for treating cancer and other diseases in which inhibition of telomerase activity can ameliorate disease symptoms or prevent or treat the disease relate to compounds characterized by the following structure:

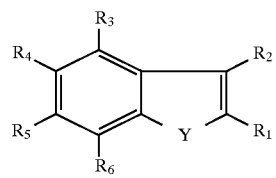

and their pharmaceutically acceptable salts. Y is selected from the group consisting of oxygen, sulfur, sulfonyl, sulfinyl, and —$NR_7$—. $R_1$ is —$TR_8$, where T is —$C(X_1)$— or —$SO_2$—, and $R_8$ is selected from the group consisting of —$OR_9$, —$NHNHSO_2R_9$, —$NHNHC(X_2)OR_9$, —$NR_9R_{10}$, —$NHNHC(X_2)NR_9R_{10}$, —$NHCR_9R_{10}C(X_2)NR_{11}R_{12}$, —$NHC(X_2)NR_9R_{10}$, and the piperazinyl moiety shown below:

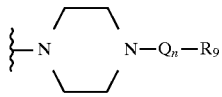

where n is 0 or 1, and $Q_n$, for n=1, is —$SO_2$—, —$C(X_2)$— or —$C(X_2)NR_{10}$—. $R_2$–$R_6$ are selected independently from the group consisting of hydrogen, alkyl, aryl, hydroxyl, alkoxyl, aryloxyl, aralkoxyl, halogen, cyano, nitro, alkylcarbamido, arylcarbamido, dialkylcarbamido, diarylcarbamido, alkylarylcarbamido, alkylthiocarbamido, arylthiocarbamido, dialkylthiocarbamido, diarylthiocarbamido, alkylarylthiocarbamido, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, alkylcarbonyloxy, arylcarbonyloxy, carboxyl, alkoxycarbonyl, aryloxycarbonyl, sulfo, alkylsulfonylamido, arylsulfonylamido, alkylsulfonyl, arylsulfonyl, alkylsulfinyl, and arylsulfinyl. $X_1$ and $X_2$ are selected independently from the group consisting of oxygen, and sulfur. $R_7$–$R_{12}$ are selected independently from the group consisting of hydrogen, alkyl, aryl, aralkyl, heterocycle, and heterocyclealkyl.

22 Claims, No Drawings

OTHER PUBLICATIONS

STN search results for: Wright et al., Preparation of 3–chlorobenzo[b]thiophene Derivatives From Cinnamic Acids, J. Heterocycl. Chem., vol. 8, No. 5, pp. 711–714, 1971.

STN search results for: Mohamadi et al., Antineoplastic Bicyclic Sulfonylureas, Bioorg. Med. Chem. Lett., vol. 2, No. 9, pp. 987–992, 1992.

STN search results for: Kutschy et al., New Synthesis of N–acylurea Derivatives, Collect. Czech. Chem. Commun., vol. 58, No. 3, pp. 575–587, 1993.

STN search results for: Bassin et al., Chlorosulfonation of Some Polynuclear Heterocyclic Compounds, Phosphorus, Sulfur Silicon Relat. Elem., vol. 72, No. 1–4, pp. 157–170, 1992.

STN search results for: EP 512 570, Nov. 1992.

AboulWafa et al., Benzo[b]thiophenes, Part I: Synthesis and Antimicrobial Activity of Benzo[b]thienyl—1,3,4–oxadiazole,—1,2,4–triazoline, and—thiazoline Derivatives, Arch. Pharm., 325, pp. 123–127, 1992.

Steven L. Castle et al., "The Synthesis of Monomethoxy[1]benzothieno[2,3–c]quinolines," Heterocyclic Chem., 24, 1103–1108 (1987).

David T. Connor et al., "Novel Benzothiophene—Benzofuran—, and Naphthalenecarboxamidotetrazoles as Potential Antiallergy Agents," Journal of Medicinal Chemistry, vol. 35, No. 5, pp. 958–965 (1992).

Tatsuo Higa and Arnold J. Krubsack, "Oxidations by Thionyl Chloride. 8. A convenient Synthesis of Benzo[b]thiophenes from Carboxylic Acids and Ketones," J. Org. Chem., vol. 41, No. 21, pp. 3399–3403 (1976).

Tatsuo Higa and Arnold J. Krubsack, "Oxidations By Thionyl Chloride, VI. Mechanism of the Reaction with Cinnamic Acids," J. Org. Chem, vol. 40, No. 21, pp. 3037–3045 (1975).

Nam W. Kim et al., "Specific Association of Human Telomerase Activity with Immortal Cells and Cancer," Science vol. 266, pp. 2011–2014 (1994).

Walter Ried et al., "Synthese von substituierten Benzol[b]thiophenen," Liebigs Ann. Chem, pp. 1424–1427 (1980).

T. de Lange, "Telomerase Activity in Human Tumors", Tumor Telomeres; Telomeres (1995), pp. 283–284.

TELOMERASE INHIBITORS

CROSS REFERENCE TO RELATED U.S. PATENT APPLICATIONS

This Application claims priority under 35 U.S.C. § 120 as a continuation-in-part of U.S. patent applications Ser. Nos. 08/425,043 and 08/424,813, both of which were filed on Apr. 18, 1995, now U.S. Pat. No. 5,760,062 and U.S. Pat. No. 5,703,116 respectively, and both of which are incorporated herein by reference for all purposes.

NOTICE OF U.S. GOVERNMENT RIGHTS

A portion of the work described herein was funded in part by SBIR Grant No. 1 R43 CA65178-01. The U.S. Government may therefore have certain rights relating to this invention.

BACKGROUND OF THE INVENTION

1. The Field of the Invention

The present invention relates to human telomerase, a ribonucleoprotein enzyme involved in human telomere DNA synthesis, and to compounds that inhibit telomerase activity. The invention provides methods, compounds and compositions relating to the fields of molecular biology, chemistry, pharmacology, oncology and medicinal and diagnostic technology.

2. Description of Related Disclosures

The war on cancer has raged for over two decades. Yet, despite the expenditure of over a billion dollars for research and development of new technologies to diagnose and treat malignancies, the age-adjusted cancer mortality rate in the U.S. has remained largely unchanged for the past forty years. Indeed, if current epidemiological trends continue, it appears likely that cancer will overtake cardiovascular disease as the leading cause of death in the United States.

To be sure, some battles have been won and much has been learned about the enemy. A few cancers (e.g., Hodgkin's disease) are now considered curable, and treatment regimes for many other cancers have improved over the last decade. In addition, there has been an explosion of information describing the regulatory mechanisms involved with the onset of malignancy, including the roles of growth factors, receptors, signal transduction pathways, oncogenes, and tumor suppressor genes in the control of cell growth and differentiation. However, these successes are overshadowed by the fact that cancer is a highly heterogeneous disease in which profound differences exist in the mechanisms by which different cell types become malignant. Thus, although we know more about the mechanisms by which cells become malignant than ever before, each type of cancer presents a unique set of problems in terms of treatment.

Because the cellular mechanisms leading to cancer are so heterogeneous, research on such mechanisms is unlikely to yield a general approach to cancer treatment that is effective and well tolerated by cancer patients. Presently, a variety of non-specific treatment modalities are available, including surgery, radiation, and a variety of cytoreductive and hormone-based drugs, used alone or in combination. Some oncolytic drugs are also available, but the efficacy of these drugs varies among cancer types. Thus, patients suffering from cancer often are forced to undergo treatments that are highly non-specific and highly toxic. Commonly, the toxicity of the treatments produces severe side effects, including nausea and vomiting, hair loss, diarrhea, fatigue, ulcerations and the like, which severely impact the patient's quality of life. In some cases, the impact on the patient's quality of life can be so great that the patient is unable to continue the full course of therapy or opts out of treatment entirely.

Recently, however, an understanding of the mechanisms by which normal cells reach the state of senescence, i.e., the loss of proliferative capacity that cells normally undergo in the cellular aging process, has begun to emerge. The DNA at the ends, or telomeres, of the chromosomes of eukaryotes usually consists of tandemly repeated simple sequences. Scientists have long known that telomeres have an important biological role in maintaining chromosome structure and function. More recently, scientists have speculated that the cumulative loss of telomeric DNA over repeated cell divisions may act as a trigger of cellular senescence and aging, and that the regulation of telomerase, an enzyme involved in the maintenance of telomere length, may have important biological implications. See Harley, 1991, *Mutation Research*, 256:271–282, incorporated herein by reference.

Telomerase is a ribonucleoprotein enzyme that synthesizes one strand of the telomeric DNA using as a template a sequence contained within the RNA component of the enzyme. See Blackburn, 1992, *Annu. Rev. Biochem.*, 61:113–129, incorporated herein by reference. Methods for detecting telomerase activity, as well as for identifying compounds that regulate or affect telomerase activity, together with methods for therapy and diagnosis of cellular senescence and immortalization by controlling telomere length and telomerase activity, have also been described. See, Feng, et al., 1995, *Science*, 269:1236–1241; Kim, et al., 1994, *Science*, 266:2011–2014; PCT patent publication No. 93/23572, published Nov. 25, 1993; U.S. patent application Ser. Nos. 08/288,501, filed Aug. 10, 1994; Ser. No. 08/330,123, filed Oct. 27, 1994; Ser. No. 08/272,102, filed Jul. 7, 1994; Ser. No. 08/255,774, filed Jun. 7, 1994; Ser. No. 08/315,214 and Ser. No. 08/315,216, both of which were filed Sep. 28, 1994; Ser. Nos. 08/151,477 and 08/153,051, both of which were filed Nov. 12, 1993; Ser. No. 08/060,952, filed May 13, 1993; and Ser. No. 08/038,766, filed Mar. 24, 1993. Each of the foregoing patent applications and references is incorporated herein by reference.

The identification of compounds that inhibit telomerase activity provides important benefits to efforts at treating human disease. Compounds that inhibit telomerase activity can be used to treat cancer, as cancer cells express telomerase activity and normal human somatic cells do not express telomerase activity at biologically relevant levels (i.e., at levels sufficient to maintain telomere length over many cell divisions). Unfortunately, few such compounds have been identified and characterized. Hence, there remains a need for compounds that act as telomerase inhibitors and for compositions and methods for treating cancer and other diseases in which telomerase activity is present abnormally. The present invention meets these and other needs.

SUMMARY OF THE INVENTION

The present invention provides methods, compounds and compositions that are highly unique, specific, and effective for treating malignant conditions by targeting cells having telomerase activity. The methods, compounds, and compositions of the invention can be applied to a wide variety of malignant cell types and avoid the problems inherent in current cancer treatment modalities which are non-specific and excessively toxic.

In a first aspect, the present invention provides methods and compositions for treating cancer in which a therapeutically effective amount of a compound having the formula shown (including a pharmaceutically acceptable salt thereof) below is administered to a mammal.

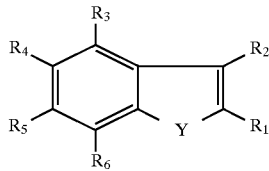

Compound I

In Compound I, Y is selected from the group consisting of oxygen, sulfur, sulfonyl, sulfinyl, and —$NR_7$—. $R_1$ is —$TR_8$, where T is —$C(X_1)$— or —$SO_2$—, and $R_8$ is selected from the group consisting of —$OR_9$, —$NHNHSO_2R_9$, —$NHNHC(X_2)OR_9$, —$NR_9R_{10}$, —$NHNHC(X_2)NR_9R_{10}$, —$NHCR_9R_{10}C(X_2)NR_{11}R_{12}$, —$NHC(X_2)NR_9R_{10}$, and the piperazinyl moiety shown below:

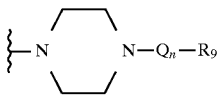

where n is 0 or 1, and $Q_n$, for n=1, is —$SO_2$—, —$C(X_2)$— or —$C(X_2)NR_{10}$—. $R_2$–$R_6$ are select independently from the group consisting of hydrogen, alkyl, aryl, hydroxyl, alkoxyl, aryloxyl, aralkoxyl, halogen, cyano, nitro, alkylcarbamido, arylcarbamido, dialkylcarbamido, diarylcarbamido, alkylarylcarbamido, alkylthiocarbamido, arylthiocarbamido, dialkylthiocarbamido, diarylthiocarbamido, alkylarylthiocarbamido, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, alkylcarbonyloxy, arylcarbonyloxy, carboxyl, alkoxycarbonyl, aryloxycarbonyl, sulfo, alkylsulfonylamido, arylsulfonylamido, alkylsulfonyl, arylsulfonyl, alkylsulfinyl, and arylsulfinyl. $X_1$, and $X_2$ are selected independently from the group consisting of oxygen, and sulfur. $R_7$–$R_{12}$ are selected independently from the group consisting of hydrogen, alkyl, aryl, aralkyl, heterocycle, and heterocyclealkyl.

In another aspect, the present invention provides novel compounds having the structure of Compound I above where T is —$C(X_1)$— thereby defining $R_1$ as —$C(X_1)R_8$. However, with respect to the compounds of the invention, if $R_8$ is —$NHNHC(X_2)NR_9R_{10}$ when T is —$C(X_1)$—, i.e., $R_1$ is —$C(X_1)NHNHC(X_2)NR_9R_{10}$, $R_{10}$ is not methyl, phenyl or phenyl substituted at the para position with methoxy or chloro when Y is sulfur, $X_1$ is oxygen, $X_2$ is sulfur, $R_2$ is chloro, $R_3$, $R_4$, $R_6$, and $R_9$ are hydrogen and $R_5$ is methoxy or hydrogen. Also, when T is —$C(X_1)$—, $R_8$ is —NHNHC$(X_2)NR_9R_{10}$, and Y is sulfur, $X_1$ is oxygen, $X_2$ is sulfur, $R_2$ is chloro, and $R_3$–$R_6$ and $R_9$ are hydrogen, $R_{10}$ is not para-methylphenyl, unsubstituted benzyl or unsubstituted allyl.

Preferred embodiments of the present invention include those derivatives of Compound I for which T is —$C(X_1)$— and $R_8$ is —$NHNHC(X_2)NR_9R_{10}$, $R_9$ is hydrogen, $X_1$ is oxygen, $X_2$ is sulfur, $R_{10}$ is phenyl or substituted phenyl, and $R_2$–$R_6$ are selected independently from the group consisting of hydrogen, amino, nitro, cyano, alkyl, aryl, halogen, alkoxyl, aryloxyl, aralkoxyl, arylthiocarbamido, alkylthio, and arylthio. Within these preferred derivatives of Compound I, those compounds for which T is —$C(X_1)$— and $R_8$ is —$NHNHC(X_2)NR_9R_{10}$, $R_9$ is hydrogen, $X_1$ is oxygen, $X_2$ is sulfur, $R_2$–$R_4$ are chloro, $R_5$ and $R_6$ are hydrogen, Y is sulfur, and $R_{10}$ is selected from the group consisting of 2, 3, 4, 5-tetrachlorophenyl, 2,3-dichlorophenyl, 2,4-dichlorophenyl, 2,5-dichlorophenyl, 2,3,4-trichlorophenyl, 2,5-dibromophenyl, 3,5-bis(trifluoromethyl)phenyl, 2-(4-methylphenylthio)phenyl, 2-naphthyl, 2,4,5-trichlorophenyl, 2,4,6-trichlorophenyl, and 4-chlorophenyl have been found to have strong anti-telomerase activity.

In still another aspect, the present invention provides telomerase-inhibiting benzo[b]dioxane derivatives having the general structure shown below.

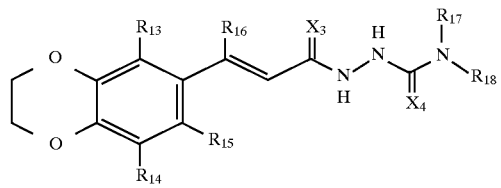

In this compound, $R_{13}$–$R_{15}$ are selected independently from the group consisting of hydrogen, alkyl, aryl, hydroxyl, alkoxyl, aryloxyl, halogen, cyano, nitro, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, alkylcarbonyloxy, arylcarbonyloxy, carboxyl, alkoxycarbonyl, aryloxycarbonyl, sulfo, alkylsulfonyl, arylsulfonyl, alkylsulfinyl, and arylsulfinyl. $R_{16}$–$R_{18}$ are selected independently from the group consisting of hydrogen, alkyl, aryl, aralkyl, heterocycle, and heterocyclealkyl. Finally, $X_3$ and $X_4$ are selected independently from the group consisting of oxygen and sulfur. More specific embodiments having useful anti-telomerase activity include those for which $X_3$ is oxygen, $X_4$ is sulfur, $R_{13}$–$R_{17}$ are hydrogen, and $R_{18}$ is phenyl or substituted phenyl, and, more particularly, where $R_{18}$ is phenyl substituted with halogen, especially chlorine.

In still another aspect, the present invention provides N-carbazoylaniline derivative having the structure shown below.

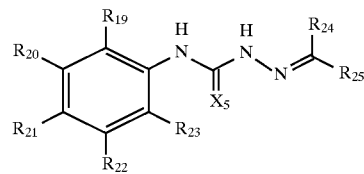

In this compound $R_{19}$–$R_{23}$ are selected independently from the group consisting of hydrogen, alkyl, aryl, hydroxyl, alkoxyl, aryloxyl, halogen, cyano, nitro, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, alkylcarbonyloxy, arylcarbonyloxy, carboxyl, alkoxycarbonyl, aryloxycarbonyl, sulfo, alkylsulfonyl, arylsulfonyl, alkylsulfinyl, and arylsulfinyl. In addition, $R_{20}$ and $R_2$, can also serve as points of attachment for the group -$Z_1$-$Z_2$-$Z_3$-$Z_4$-, where $Z_1$–$Z_4$ are selected independently from the group consisting of methine and quaternary carbon to form in combination with the phenyl ring to which $R_{19}$–$R_{23}$ are attached a naphthyl or substitued naphthyl group. $R_{24}$ and $R_{25}$ are selected independently from the group consisting of hydrogen, alkyl, aryl, aralkyl, heterocycle, and heterocyclealkyl. $X_5$ is selected from the group consisting of oxygen and sulfur. Compounds of the general formula that have useful anti-telomerase activity include those for which $X_5$ is sulfur, $R_{19}$ and $R_{20}$ independently are hydrogen or chloro, $R_{21}$ is chloro, $R_{22}$–$R_{24}$ are hydrogen, and $R_{25}$ is heteroaryl or aryl.

The above-illustrated derivatives have many valuable uses as inhibitors of deleterious telomerase activity, most importantly, the use to treat cancer in humans. The pharmaceutical compositions of this invention can be employed in treatment regimens in which cancer cells are killed, in vivo, as can be demonstrated by the use of telomerase inhibitors of the invention to kill cancer cells ex vivo. Thus, this invention provides therapeutic compositions for treating cancer, and methods for treating cancer in humans and other mammals (e.g., cows, horses, sheep, steer, pigs and animals of veterinary interest such as cats and dogs).

These and other features of the invention will be described in detail below with reference to the associated structures and tables.

DESCRIPTION OF SPECIFIC EMBODIMENTS

I. Definitions

The term "alkyl" as used herein refers to a straight, branched, or cyclic hydrocarbon chain fragment or radical containing between about one and about twenty carbon atoms, more preferably between about one and about ten carbon atoms (e.g., methyl, ethyl, n-propyl, iso-propyl, cyclopropyl, n-butyl, iso-butyl, tert-butyl, cyclobutyl, adamantyl, noradamantyl and the like). Straight, branched, or cyclic hydrocarbon chains having eight or fewer carbon atoms will also be referred to herein as "lower alkyl". The hydrocarbon chains may further include one or more degrees of unsaturation, i.e., one or more double or triple bonds (e.g., vinyl, propargyl, allyl, 2-buten-1-yl, 2-cyclopenten-1-yl, 1,3-cyclohexadien-1-yl, 3-cyclohexen-1-yl and the like). Alkyl groups containing double bonds such as just described will also be referred to herein as "alkenes". Similarly, alkyl groups having triple bonds will also be referred to herein as "alkynes". However, as used in context with respect to cyclic alkyl groups, the combinations of double and/or triple bonds do not include those bonding arrangements that render the cyclic hydrocarbon chain aromatic.

In addition, the term "alkyl" as used herein further includes one or more substitutions at one or more carbon atoms of the hydrocarbon fragment or radical. Such substitutions include, but are not limited to: aryl; heterocycle; halogen (to form, e.g., trifluoromethyl, —$CF_3$); nitro (—$NO_2$); cyano (—CN); hydroxyl (also referred to herein as "hydroxy"), alkoxyl (also referred herein as alkoxy) or aryloxyl (also referred to herein as "aryloxy", —OR); thio or mercapto, alkyl, or arylthio (—SR); amino, alkylamino, arylamino, dialkyl- or diarylamino, or arylalkylamino (—NRR'); aminocarbonyl, alkylaminocarbonyl, arylaminocarbonyl, dialkylaminocarbonyl, diarylaminocarbonyl or arylalkylaminocarbonyl (—C(O)NRR'); carboxyl, or alkyl- or aryloxycarbonyl (—C(O)OR); carboxaldehyde, or aryl- or alkylcarbonyl (—C(O)R); iminyl, aryl- or alkyliminyl (—C(=NR)R'); sulfo (—$SO_2$OR); alkyl- or arylsulfonyl (—$SO_2$R); carbamido (—HNC(=O)NRR'); or thiocarbamido (—HNC(=S)NRR'); where R and R' independently are hydrogen, aryl or alkyl as defined herein. Substituents including heterocyclic groups (i.e., heterocycle, heteroaryl, and heteroaralkyl) are defined by analogy to the above-described terms. For example, the term "heterocycleoxy" refers to the group —OR, where R is heterocycle as defined below.

The term "methylene" refers to the group —$CH_2$—.

The term "methine" refers to a methylene group for which one hydrogen atom has been replaced by a substituent as described above. The term "methine" can also refer to a methylene group for which one hydrogen atom is replaced by bond to form an $sp^2$-hybridzed carbon center (i.e., —CH=).

The term "quarternary carbon" refers to a methylene group in which both hydrogen atoms are replaced by two independent substituents as described above. The term "quarternary carbon" can also refer to a methylene group for which one hydrogen atom is replaced by bond to form an $sp^2$-hybridzed carbon center and the other hydrogen atom is replaced by a substituent as described above (i.e., —CR=), or a methylene group in which both hydrogen atoms are replaced by bonds to form an sp-hybridized carbon center (i.e., —C≡).

The term "halogen" as used herein refers to the substituents fluoro, bromo, chloro, and iodo.

The term "carbonyl" as used herein refers to the functional group —C(O)—. However, it will be appreciated that this group may be replaced with well-known groups that have similar electronic and/or steric character, such as thiocarbonyl (—C(S)—); sulfinyl (—S(O)—); sulfonyl (—$SO_2$—), phosphonyl (—$PO_2$—), and methylene (—C($CH_2$)—). Other carbonyl equivalents will be familiar to those having skill in the medicinal and organic chemical arts.

The term "aryl" as used herein refers to cyclic aromatic hydrocarbon chains having twenty or fewer carbon atoms, e.g., phenyl, naphthyl, biphenyl and anthracenyl. One or more carbon atoms of the aryl group may also be substituted with, e.g.: alkyl; aryl; heterocycle; halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; carboxaldehyde, or aryl- or alkylcarbonyl; iminyl, or aryl- or alkyliminyl; sulfo; alkyl- or arylsulfonyl; hydroximinyl, or aryl- or alkoximinyl; carbamido; or thiocarbamido. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heterocycleoxy, heteroaryloxy, and heteroaralkylthio) are defined by analogy to the above-described terms.

The term "aralkyl" as used herein refers to an aryl group that is joined to a parent structure by an alkyl group as described above, e.g., benzyl, α-methylbenzyl, phenethyl, and the like.

The term "heterocycle" as used herein refers to a cyclic alkyl group or aryl group as defined above in which one or more carbon atoms have been replaced by a non-carbon atom, especially nitrogen, oxygen, or sulfur. Non-aromatic heterocycles will also be referred to herein as "cyclic heteroalkyl". Aromatic heterocycles are also referred to herein as "heteroaryl". For example, such groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridazinyl, triazinyl, piperidinyl, morpholinyl, thiomorpholinyl, pyrazinyl, piperazinyl, pyrimidinyl, naphthyridinyl, benzofuranyl, benzothienyl, indolyl, indolinyl, indolizinyl, indazolyl, quinolizinyl, quinolinyl, isoquinolinyl, cinnolinyl, phthalazinyl, quinazolinyl, quinoxalinyl, pteridinyl, quinuclidinyl, carbazolyl, acridiniyl, phenazinyl, phenothiazinyl, phenoxazinyl, purinyl, benzimidazolyl, benzthiazolyl, and benzoxazolyl.

The above heterocyclic groups may further include one or more substituents at one or more carbon and/or non-carbon atoms of the heteroaryl group, e.g.: alkyl; aryl; heterocycle; halogen; nitro; cyano; hydroxyl, alkoxyl or aryloxyl; thio or mercapto, alkyl- or arylthio; amino, alkyl-, aryl-, dialkyl-diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; carboxaldehyde, or aryl- or alkylcarbonyl; iminyl, or aryl- or alkyliminyl; sulfo; alkyl- or arylsulfonyl; hydroximinyl, or aryl- or alkoximinyl; carbamido; or thiocarbamido. In addition, two or more alkyl substituents may be combined to form fused heterocycle-alkyl or heterocycle-aryl ring systems. Substituents including heterocyclic groups (e.g., heterocycleoxy, heteroaryloxy, and heteroaralkylthio) are defined by analogy to the above-described terms.

The term "heterocyclealkyl" refers to a heterocycle group that is joined to a parent structure by one or more alkyl groups as described above, e.g., 2-piperidylmethyl, and the like. The term "heteroaralkyl" as used herein refers to a heteroaryl group that is joined to a parent structure by one or more alkyl groups as described above, e.g., 2-thienylmethyl, and the like.

II. Telomerase Inhibitors

As noted above, the immortalization of cells involves inter alia the activation of telomerase. More specifically, the connection between telomerase activity and the ability of many tumor cell lines, including skin, connective tissue, adipose, breast, lung, stomach, pancreas, ovary, cervix, uterus, kidney, bladder, colon, prostate, central nervous system (CNS), retina and blood tumor cell lines, to remain immortal has been demonstrated by analysis of telomerase activity (Kim, et al., incorporated herein by reference above). This analysis, supplemented by data that indicates that the shortening of telomere length can provide the signal for replicative senescence in normal cells, see PCT Application No. 93/23572 (incorporated herein by reference above), demonstrates that inhibition of telomerase activity can be an effective anti-cancer therapy. Thus, telomerase activity can prevent the onset of otherwise normal replicative senescence by preventing the normal reduction of telomere length and the concurrent cessation of cell replication that occurs in normal somatic cells after many cell divisions. In cancer cells, where the malignant phenotype is due to loss of cell cycle or growth controls or other genetic damage, an absence of telomerase activity permits the loss of telomeric DNA during cell division, resulting in chromosomal rearrangements and aberrations that lead ultimately to cell death. However, in cancer cells having telomerase activity, telomeric DNA is not lost during cell division, thereby allowing the cancer cells to become immortal, leading to a terminal prognosis for the patient. Agents capable of inhibiting telomerase activity in tumor cells offer therapeutic benefits with respect to a wide variety of cancers and other conditions (e.g., fungal infections) in which immortalized cells having telomerase activity are a factor in disease progression or in which inhibition of telomerase activity is desired for treatment purposes. The telomerase inhibitors of the invention can also be used to inhibit telomerase activity in germ line cells, which may be useful for contraceptive purposes.

Thus, in one aspect, the present invention provides compounds that can serve in the war against cancer as important weapons against many types of malignancies. In particular, the compounds of the present invention can provide a highly general method of treating many-if not most-malignancies, as demonstrated by the highly varied human tumor cell lines and tumors having telomerase activity. More importantly, the compounds of the present invention can be effective in providing treatments that discriminate between malignant and normal cells to a high degree, avoiding many of the deleterious side-effects present with most current chemotherapeutic regimes which rely on agents that kill dividing cells indiscriminately.

In one aspect, the present invention provides pharmaceutical compositions and methods relating to compounds having the general structure shown as Compound I below:

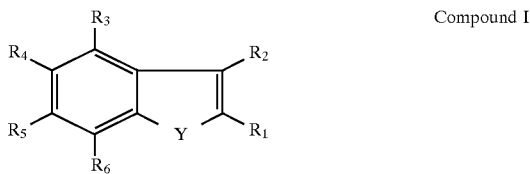

Compound I and its pharmaceutically acceptable salts. In Compound I above, Y is selected from the group consisting of oxygen, sulfur, sulfonyl, sulfinyl, and —$NR_7$—. $R_1$ is —$TR_8$, where T is —$SO_2$— or —$C(X_1)$— and $R_8$ is selected from the group consisting of —$OR_9$, —$NHNHSO_2R_9$, —$NHNHC(X_2)OR_9$, —$NR_9R_{10}$, —$NHNHC(X_2)NR_9R_{10}$, —$NHCR_9R_{10}C(X_2)NR_{11}R_{12}$, —$NHC(X_2)NR_9R_{10}$, and the piperazinyl moiety shown below:

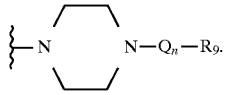

In the piperazinyl moiety shown above, n is 0 or 1, and $Q_n$, for n=1, is —$SO_2$—, —$C(X_2)$— or —$C(X_2)NR_{10}$—. $R_2$–$R_6$ are selected independently from the group consisting of hydrogen, alkyl, aryl, hydroxyl, alkoxyl, aryloxyl, aralkoxyl, halogen, cyano, nitro, alkylcarbamido, arylcarbamido, dialkylcarbamido, diarylcarbamido, alkylarylcarbamido, alkylthiocarbamido, arylthiocarbamido, dialkylthiocarbamido, diarylthiocarbamido, alkylarylthiocarbamido, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, alkylcarbonyloxy, arylcarbonyloxy, carboxyl, alkoxycarbonyl, aryloxycarbonyl, sulfo, alkylsulfonylamido, arylsulfonamido, alkylsulfonyl, arylsulfonyl, alkylsulfinyl, and arylsulfinyl. $X_1$ and $X_2$ are selected independently from the group consisting of oxygen and sulfur. $R_7$–$R_{12}$ are selected independently from the group consisting of hydrogen, alkyl, aryl, aralkyl, heterocycle, and heterocyclealkyl.

The present invention also provides novel compounds having the structure of Compound I. However, with respect to the compounds of the invention, if T is —$C(X_1)$— and $R_8$ is —$NHNHC(X_2)NR_9R_{10}$ (i.e., $R_1$ is —$C(X_1)NHNHC(X_2)NR_9R_{10}$), $R_{10}$ is not methyl, phenyl or phenyl substituted at the para position with methoxy or chloro when Y is sulfur, $X_1$ is oxygen, $X_2$ is sulfur, $R_2$ is chloro, $R_3$, $R_4$, $R_6$, and $R_9$ are hydrogen, and $R_5$ is methoxy or hydrogen. Also, when T is —$C(X_1)$—, $R_8$ is —$NHNHC(X_2)NR_9R_{10}$, Y is sulfur, $X_1$ is oxygen, $X_2$ is sulfur, $R_2$ is chloro, and $R_3$–$R_6$ and $R_9$ are hydrogen, $R_{10}$ is not para-methylphenyl, unsubstituted benzyl or unsubstituted allyl.

In one embodiment, the present invention provides derivatives of Compound I above in which T is —$C(X_1)$—, $R_8$ is —NHNHC($X_2$)N$R_9R_{10}$, $R_9$ is hydrogen, and $X_1$ and $X_2$ independently are oxygen or sulfur. More particular embodiments having this substituent pattern are those in which $R_{10}$ is aryl, aralkyl, or heteroaryl. Still more particular are those embodiments for which T, $R_8$, $R_9$, $X_1$ and $X_2$ are as just recited and $R_{10}$ is phenyl or substituted phenyl. Yet more specific embodiments are those in which T is —C($X_1$)—, $R_8$ is —NHNHC($X_2$)N$R_9R_{10}$, $R_9$ is hydrogen, $X_1$ and $X_2$ independently are oxygen or sulfur, $R_{10}$ is phenyl or substituted phenyl, and $R_2$–$R_6$ are selected independently from the group consisting of hydrogen, amino, nitro, cyano, alkyl, aryl, halogen, alkoxyl, aryloxyl, aralkoxyl, arylthiocarbamido, alkylthio, and arylthio.

More particular embodiments of Compound I above are those in which T is —C($X_1$)—, $R_8$ is —NHNHC($X_2$)N$R_9R_{10}$, $R_9$ is hydrogen, $X_1$ is oxygen, $X_2$ is sulfur, $R_{10}$ is phenyl or substituted phenyl, and $R_2$–$R_6$ are selected independently from the group consisting of hydrogen, amino, nitro, cyano, alkyl, aryl, halogen, alkoxyl, aryloxyl, arylthiocarbamido, aralkoxyl, alkylthio, and arylthio. Still more particular embodiments of Compound I provided by the present invention are those having the substituents just recited, but in which $R_2$ is hydrogen or halogen. Other derivatives of Compound I provided by the present invention are those for which $R_1$ is —C($X_1$)NHNHC($X_2$)N$R_9R_{10}$, $R_9$ is hydrogen, $X_1$ is oxygen, $X_2$ is sulfur, $R_{10}$ is phenyl or substituted phenyl, $R_2$ is hydrogen or halogen, $R_3$–$R_6$ are selected independently from the group consisting of hydrogen, amino, nitro, cyano, alkyl, aryl, halogen, alkoxyl, aryloxyl, aralkoxyl, alkylthio, arylthiocarbamido, and arylthio, and Y is sulfur.

Derivatives of Compound I having useful anti-telomerase properties include those in which T is —C($X_1$)—, $R_8$ is —NHNHC($X_2$)N$R_9R_{10}$, $R_9$ is hydrogen, $X_1$ is oxygen, $X_2$ is sulfur, $R_{10}$ is phenyl or substituted phenyl, and $R_3$–$R_6$ are selected independently from the group consisting of hydrogen, amino, nitro, cyano, alkyl, aryl, halogen, alkoxyl, aryloxyl, aralkoxyl, alkylthio, arylthiocarbamido, and arylthio, $R_2$ is hydrogen, and Y is sulfur. In particular, the derivative Compound I for which T is —C($X_1$)—, $R_8$ is —NHNHC($X_2$)N$R_9R_{10}$, Y is sulfur, $R_9$ is hydrogen, $X_1$ is oxygen, $X_2$ is sulfur, $R_2$, $R_3$, $R_5$, and $R_6$ are hydrogen, $R_4$ is N-(4-methylphenyl)thiocarbamido, and $R_{10}$ is 2,5-dichlorophenyl (Compound II) has been found to have good anti-telomerase activity as shown in Table 1 below.

Other derivatives of Compound I having useful telomerase-inhibiting properties provided by the present invention include those for which T is —C($X_1$)—, $R_8$ is —NHNHC($X_2$)N$R_9R_{10}$, $R_2$, $R_3$, $R_5$, $R_6$, and $R_9$ are hydrogen, $R_4$ is N-[2-(4-methylphenylthio)phenyl] thiocarbamido, and $R_{10}$ is 2-(4-methylphenylthio)phenyl (Compound III), and those for which T is —C($X_1$)—, $R_8$ is —NHNHC($X_2$)N$R_9R_{10}$, $R_2$, $R_3$, $R_5$, $R_6$ and $R_9$ are hydrogen, $R_4$ is N-(3-methylphenyl)thiocarbamido, and $R_{10}$ is 3,5-bis(trifluoromethyl)phenyl (Compound IV), 2-(4-methylphenylthio)phenyl (Compound V), or 4-(methylthio) phenyl (Compound VI).

In another embodiment of Compound I provided by the present invention, T is —C($X_1$)—, $R_8$ is —NHNHC($X_2$)N$R_9R_{10}$, $R_2$–$R_6$ and $R_9$ are hydrogen, $X_1$ is oxygen, $X_2$ is sulfur, $R_{10\ is}$ 2,5-dichlorophenyl, and Y is sulfur (Compound VII). A particularly useful telomerase inhibitor is one for which $R_1$ is —C($X_1$)NHNHC($X_2$)N$R_9R_{10}$, $R_2$–$R_5$ and $R_9$ are hydrogen, $X_1$ is oxygen, $X_2$ is sulfur, $R_{10}$ is selected from the group consisting of 2,4,5-trichlorophenyl, 2,3,4,5-tetrachlorophenyl, and 2-(4-methylphenylthio)phenyl, $R_6$ is fluoro, and Y is sulfur (Compounds VIII, IX, and X, respectively).

Also provided by the present invention are compounds derived from Compound I in which T is —C($X_1$)—, $R_8$ is —NHNHC($X_2$)N$R_9R_{10}$, $R_2$, $R_4$–$R_6$, and $R_9$ are hydrogen, $X_1$ is oxygen, $X_2$ is sulfur, $R_3$ is chloro, Y is sulfur, and $R_{10}$ is selected from the group consisting of 2,4,5-trichlorophenyl (Compound XI), 2,3,4,5-tetrachlorophenyl (Compound XII), 2,5-dibromophenyl (Compound XIII), 2,3,4-trichlorophenyl (Compound XIV), and 2-(4-methylphenylthio)phenyl (Compound XV). Other useful derivatives of Compound I include those for which T is —C($X_1$)—, $R_8$ is —NHNHC($X_2$)N$R_9R_{10}$, $R_9$ is hydrogen, $X_1$ is oxygen, $X_2$ is sulfur, $R_2$ and $R_4$–$R_6$ are hydrogen, $R_3$ is fluoro, Y is sulfur, and $R_{10}$ is 4-(4-nitrophenylthio)phenyl (Compound XVI).

Other useful derivatives of Compound I provided by the present invention are those for which T is —C($X_1$)—, $R_8$ is —NHNHC($X_2$)N$R_9R_{10}$, $R_9$ is hydrogen, $X_1$ is oxygen, $X_2$ is sulfur, $R_{10}$ is phenyl or substituted phenyl, $R_3$–$R_6$ are selected independently from the group consisting of hydrogen, amino, nitro, cyano, alkyl, aryl, halogen, alkoxyl, aryloxyl, aralkoxyl, alkylthio, arylthiocarbamido, and arylthio, $R_2$ is halogen, and Y is sulfur. More specific derivatives of Compound I provided by the present invention having the substituent pattern just recited include for which $R_2$ is chloro, and those for which $R_2$ is chloro and $R_3$ and $R_4$ are hydrogen. More specific derivatives of Compound I are those for which T is —C($X_1$)—, $R_8$ is —NHNHC($X_2$)N$R_9R_{10}$, $R_3$, $R_4$, and $R_9$ are hydrogen, $X_1$ is oxygen, $X_2$ is sulfur, $R_{10}$ is phenyl or substituted phenyl, $R_2$ is chloro, $R_5$ is selected from the group consisting of hydrogen, amino, nitro, cyano, alkyl, aryl, halogen, alkoxyl, aryloxyl, aralkoxyl, alkylthio, arylthiocarbamido, and arylthio, $R_6$ is hydrogen or halogen, and Y is sulfur. Even more specific are those derivatives for which T is —C($X_1$)—, $R_8$ is —NHNHC($X_2$)N$R_9R_{10}$, $R_3$, $R_4$, and $R_9$ are hydrogen, $X_1$ is oxygen, $X_2$ is sulfur, $R_5$ is methoxy, $R_2$ and $R_6$ are chloro, Y is sulfur, and $R_{10}$ is 2,4,5-trichlorophenyl (Compound XVII) or 2,3,4,5-tetrachlorophenyl (Compound XVIII).

Still other derivatives of Compound I provided by the present invention are those for which T is —C($X_1$)—, $R_8$ is —NHNHC($X_2$)N$R_9R_{10}$, $R_3$, $R_4$, $R_6$, and $R_9$ are hydrogen, $X_1$ is oxygen, $X_2$ is sulfur, $R_{10}$ is phenyl or substituted phenyl, $R_2$ is chloro, $R_5$ is selected from the group consisting of hydrogen, amino, nitro, cyano, alkyl, aryl, halogen, alkoxyl, aryloxyl, aralkoxyl, alkylthio, arylthiocarbamido, and arylthio, and Y is sulfur. Of these derivatives, the derivative for which $R_5$ is hydrogen and $R_{10}$ is 2,3,4,5-tetrachlorophenyl (Compound XIX) has been found to have useful anti-telomerase properties. Still other compounds having useful telomerase-inhibiting properties are those for which T is —C($X_1$)—, $R_8$ is —NHNHC($X_2$)N$R_9R_{10}$, $R_3$, $R_4$ $R_6$, and $R_9$ are hydrogen, $X_1$ is oxygen, $X_2$ is sulfur, $R_5$ is methoxy, $R_2$ is chloro, Y is sulfur, and $R_{10}$ is 2,4,5-trichlorophenyl (Compound XX), 2,3,4,5-tetrachlorophenyl (Compound XXI), or 2,3,4-trichlorophenyl (Compound XXII).

In another embodiment, the present invention provides a compound having the general formula of Compound I in which T is —C($X_1$)—, $R_8$ is —NHNHC($X_2$)N$R_9R_{10}$, $X_1$ is oxygen, $X_2$ is sulfur, $R_{10}$ is 2,3-dichlorophenyl, $R_3$, $R_4$, $R_6$ and $R_9$are hydrogen, $R_5$ is methyl, $R_2$ is chloro, and Y is sulfur (Compound XXIII). Also provided are embodiments in which T is —C($X_1$)—, $R_8$ is —NHNHC($X_2$)N$R_9R_{10}$, $X_1$ is oxygen, $X_2$ is sulfur, $R_3$, $R_4$, $R_6$ and $R_9$ are hydrogen, $R_5$ is phenyl, $R_2$ is chloro, Y is sulfur, and $R_{10}$ is selected from the group consisting of 2,4,5-trichlorophenyl (Compound XXIV), 2,3,4,5-tetrachlorophenyl (Compound XXV), 2,3-dichlorophenyl (Compound XXVI), 2,5-dichlorophenyl (Compound XXVII), 2,5-dibromophenyl (Compound XXVIII), and 2,4,6-trichlorophenyl (Compound XXIX).

Further embodiments of the invention having the general formula shown above for Compound I, include those for which T is —C($X_1$)—, $R_8$ is —NHNHC($X_2$)N$R_9R_{10}$, $R_9$ is hydrogen, $X_1$ is oxygen, $X_2$ is sulfur, $R_2$–$R_4$ are chloro, $R_5$ and $R_6$ are hydrogen, Y is sulfur, and $R_{10}$ is selected from the group consisting of 2,3,4,5-tetrachlorophenyl (Compound XXX), 2,3-dichlorophenyl (Compound XXXI), 2,4-dichlorophenyl (Compound XXXII), 2,5-dichlorophenyl (Compound XXXIII), 2,3,4-trichlorophenyl (Compound XXXIV), 2,5-dibromophenyl (Compound XXXV), 3,5-bis(trifluoromethyl)phenyl (Compound XXXVI), 2-(4-methylphenylthio)phenyl (Compound XXXVII), 2-naphthyl (Compound XXXVIII), 2,4,5-trichlorophenyl (Compound XXXIX), 2,4,6-trichlorophenyl (Compound XL), and 4-chlorophenyl (Compound XLI).

In another aspect, the present invention includes telomerase-inhibiting benzo[b]dioxane derivatives having the general structure shown below (Compound XLII).

Compound XLII

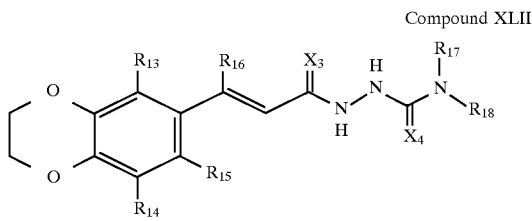

In Compound XLII, $R_{13}$–$R_{15}$ are selected independently from the group consisting of hydrogen, alkyl, aryl, hydroxyl, alkoxyl, aryloxyl, halogen, cyano, nitro, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, alkylcarbonyloxy, arylcarbonyloxy, carboxyl, alkoxycarbonyl, aryloxycarbonyl, sulfo, alkylsulfonyl, arylsulfonyl, alkylsulfinyl, and arylsulfinyl. $R_{16}$–$R_{18}$ are selected independently from the group consisting of hydrogen, alkyl, aryl, aralkyl, heterocycle, and heterocyclealkyl. Finally, $X_3$ and $X_4$ are selected independently from the group consisting of oxygen and sulfur. Embodiments of Compound XLII having useful anti-telomerase activity include those for which $X_3$ is oxygen, $X_4$ is sulfur, $R_{13}$–$R_{17}$ are hydrogen, and $R_{18}$ is phenyl or substituted phenyl, and, more particularly, phenyl substituted with halogen, especially chlorine.

In yet another aspect, the present invention provides N-carbazolylaniline derivatives having the general structure of Compound XLIII below.

Compound XLIII

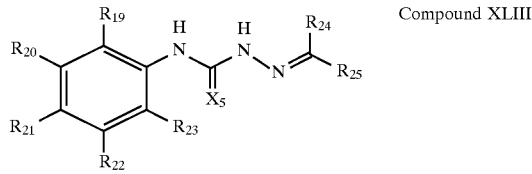

In Compound XLIII $R_{19}$–$R_{23}$ are selected independently from the group consisting of hydrogen, alkyl, aryl, hydroxyl, alkoxyl, aryloxyl, halogen, cyano, nitro, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, alkylcarbonyloxy, arylcarbonyloxy, carboxyl, alkoxycarbonyl, aryloxycarbonyl, sulfo, alkylsulfonyl, arylsulfonyl, alkylsulfinyl, and arylsulfinyl. $R_{20}$ and $R_{21}$ can also serve as points of attachment for the group -$Z_1$-$Z_2$-$Z_3$-$Z_4$-, where $Z_1$–$Z_4$ are selected independently from the group consisting of methine and quaternary carbon to form in combination with the phenyl ring to which $R_{19}$–$R_{23}$ are attached a naphthyl or substitued naphthyl group. $R_{24}$ and $R_{25}$ are selected independently from the group consisting of hydrogen, alkyl, aryl, aralkyl, heterocycle, and heterocyclealkyl. $X_5$ is selected from the group consisting of oxygen and sulfur. Compounds of the general formula of Compound XLIII above that have useful anti-telomerase activity include those for which $X_5$ is sulfur, $R_{19}$ and $R_{20}$ independently are hydrogen or chloro, $R_{21}$ is chloro, $R_{22}$–$R_{24}$ are hydrogen, and $R_{25}$ is heteroaryl or aryl.

III. Synthesis of Telomerase Inhibitors

The compounds of the present invention can be synthesized using techniques and materials known to those of skill in the art, such as described, for example, in March, ADVANCED ORGANIC CHEMISTRY $4^{th}$ Ed., (Wiley 1992); Carey and Sundberg, ADVANCED ORGANIC CHEMISTRY $3^{rd}$ Ed., Vols. A and B (Plenum 1992), and Green and Wuts, PROTECTIVE GROUPS IN ORGANIC SYNTHESIS $2^{nd}$ Ed. (Wiley 1991), each of which is incorporated herein by reference. Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Apin Chemicals, Ltd. (New Brunswick, N.J.), Ryan Scientific (Columbia, S.C.), Maybridge (Cornwall, England), Arcos (Pittsburgh, Pa.), and Trans World Chemicals (Rockville, Md.).

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon- 13 nuclear magnetic resonance ($^1$H and $^{13}$C NMR), infrared and ultraviolet spectroscopy (IR and UV), X-ray crystallography, elemental analysis (EA), HPLC and mass spectroscopy (MS) can be used as well. Methods of protection and deprotection, purification, identification and quantification are well known in the chemical arts.

Compounds of the class represented by Compound I can be synthesized using the following general procedure (Scheme 1). The use of the substituent identifiers R and R' is merely to indicate the presence of one or more substituents at the position or moiety indicated. The values of R and R' shown in Scheme 1 below can be determined by reference to the specific moieties described above in connection with the structure of Compound I.

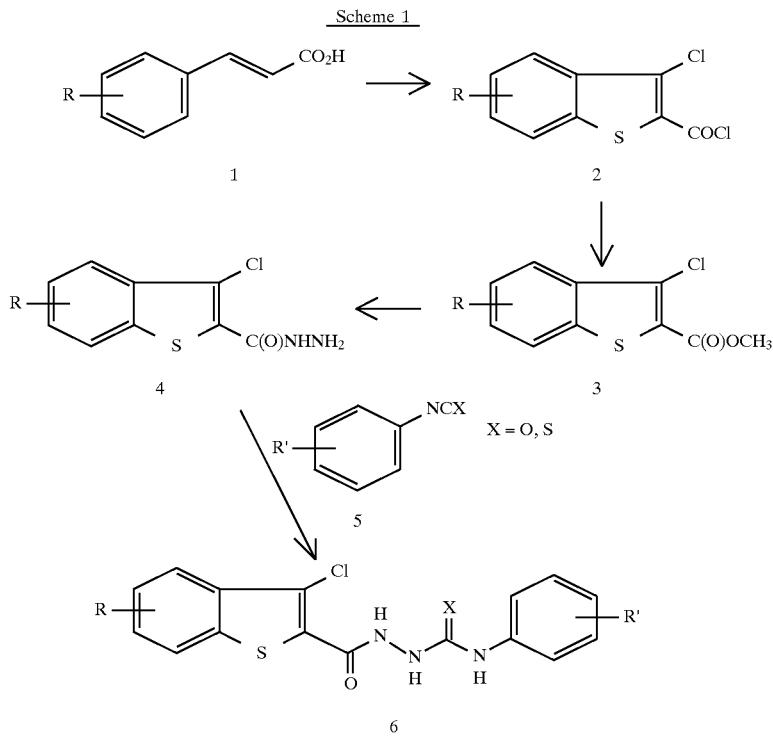

Starting from the appropriately substituted cinnamic acid 1, prepared from standard methods and procedures or purchased commercially (e.g., Aldrich), reaction with thionyl chloride under reflux provides the corresponding 3-chlorobenzo[b]thiophene-2-carbonyl chloride 2. Reaction of the acid chloride 2 using, e.g., trimethylsilyl chloride (Si(CH$_3$)$_3$Cl) and an alcohol (e.g., methanol) provides the corresponding ester 3. If the hydrazide is desired, that derivative can be prepared from the ester 3 by reaction with hydrazine in methanol to produce the hydrazide 4. Additional hydrazide derivatives, containing carbonyl or thiocarbonyl substituents on the terminal hydrazide nitrogen, can be prepared, e.g., by reaction of hydrazide 4 with an appropriately substituted isocyanate or isothiocyanate 5 to produce the corresponding addition product 6. Examples of each of the transformations outlined above are presented below. The above-described transformations are well known in the art (see, e.g., Reid, W., et al. 1980. *Liebigs. Ann. Chem.* 1424–1427; Connor, D. T., et al. 1992. *J. Med. Chem.* 35(5):958–965; Higa, T., and Krubsack, A. J. 1976. *J. Org. Chem.* 41(21): 3399–3403; and Higa, T., and Krubsack, A. J. 1976. *J. Org. Chem.* 40(21): 3037–3045, each which is incorporated herein by reference.)

The preparation of cinnamic acid 1 is illustrated in Scheme 2 below. Starting from the corresponding benzaldehyde, reaction with malonic acid (or malonic ester) with piperidine in pyridine solution at reflux provides the desired cinnamic acid 1 in good to excellent yields.

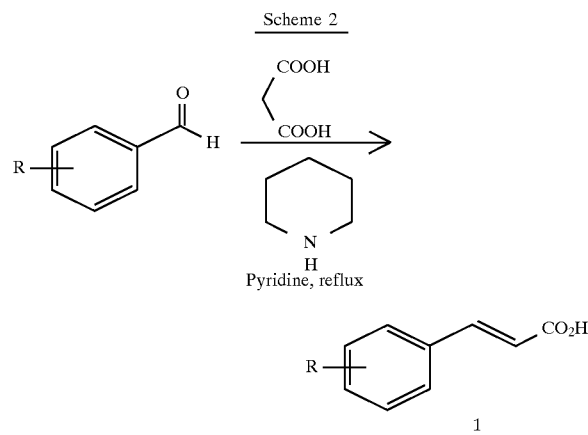

An alternative method for preparing 4- or 7-halobenzo[b]thiophene esters and 5-nitrobenzothiphene esters starting from substituted 2-fluoro and 2-chlorobenzaldehydes is shown in Scheme 3 below.

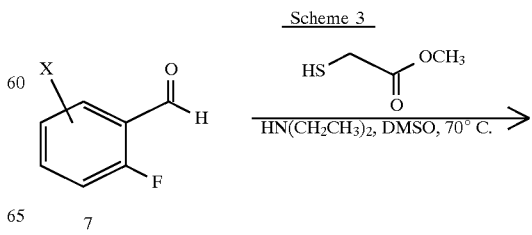

-continued
Scheme 3

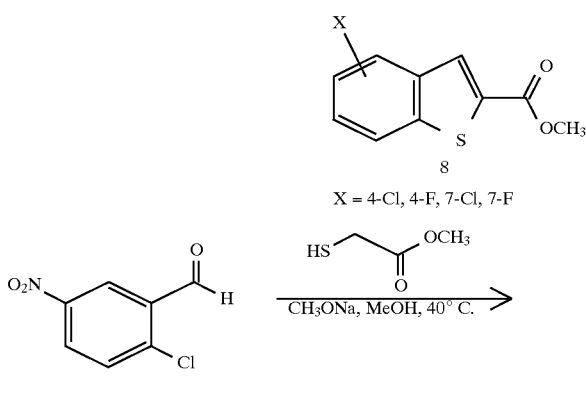

Starting from the corresponding 2-fluorobenzaldehyde 7, reaction with methyl mercaptoacetate and diethylamine in dimethylsulfoxide (DMSO) at 70° C. provides the desired 4-, or 7-halogen-substituted 2-carboxybenzo[b]thiophene methyl ester 8 in good yield. Similarly, reaction of 2-chloro-5-nitrobenzaldehyde 9 with methyl mercaptoacetate and sodium methoxide in methanol at 40° C. provides 2-carboxy-5-ntirobenzo[b]thiophene methyl ester 10. This product can be reduced using stannous chloride dihydrate in ethanol under reflux to form 2-carboxy-5-aminobenzo[b]thiophene methyl ester 11 as shown in Scheme 4 below.

Scheme 4

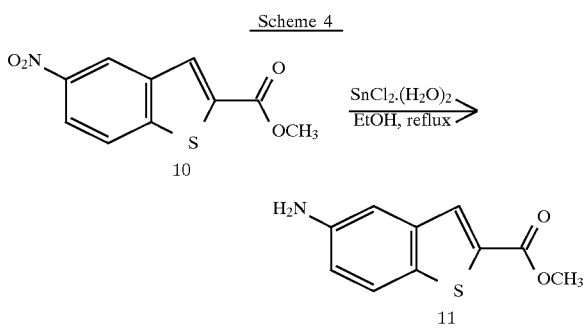

Protocols from which the individual Compounds described above can be synthesized are provided in the Examples below.

IV. Anti-Tumor Activity of the Telomerase Inhibitors of the Invention

The compounds of the present invention demonstrate inhibitory activity against in vivo, as has been and can be demonstrated as described below. The in vitro activities of the compounds of the invention can also be demonstrated using the methods described herein. As used herein, the term "in vitro" refers to tests performed using living cells in tissue culture. Such procedures are also known as "ex vivo".

One method used to identify compounds of the invention that inhibit telomerase activity involves placing cells, tissues, or preferably a cellular extract or other preparation containing telomerase in contact with several known concentrations of a test compound in a buffer compatible with telomerase activity. The level of telomerase activity for each concentration of test compound is measured and the $IC_{50}$ (the concentration of the test compound at which the observed activity for a sample preparation was observed to fall one-half of its original or a control value) for the compound is determined using standard techniques. Other methods for determining the inhibitory concentration of a compound of the invention against telomerase can be employed as will be apparent to those of skill in the art based on the disclosure herein.

With the above-described methods, $IC_{50}$ values for several of the compounds of the present invention were determined. The values reported in Table 1 below are only approximate values; more exact $IC_{50}$ values can be obtained by repetitive testing.

TABLE 1

| Compound | $IC_{50}$ ($\mu M$) | Compound | $IC_{50}$ ($\mu M$) |
|---|---|---|---|
| II | 6.0 | XXII | 8.0 |
| III | 12.0 | XXIII | 10.0 |
| IV | 23.4 | XXIV | 8.0 |
| V | 9.7 | XXV | 10.0 |
| VI | 6.4 | XXVI | 6.0 |
| VII | 10.0 | XXVII | 6.0 |
| VIII | 7.0 | XXVIII | 9.0 |
| IX | 5.0 | XXIX | 7.0 |
| X | 6.0 | XXX | 5.0 |
| XI | 10.0 | XXXI | 5.0 |
| XII | 7.0 | XXXII | 7.0 |
| XIII | 9.0 | XXXIII | 7.0 |
| XIV | 9.0 | XXXIV | 6.0 |
| XV | 9.0 | XXXV | 6.0 |
| XVI | 6.0 | XXXVI | 8.0 |
| XVII | 9.0 | XXXVII | 7.0 |
| XVIII | 15.0 | XXXVIII | 5.0 |
| XIX | 8.0 | XXXIX | 5.0 |
| XX | 9.0 | XL | 14.0 |
| XXI | 5.0 | XLI | 8.0 |

As shown in Table 1, nearly all of the compounds of the invention have strong anti-telomerase activity (i.e., an $IC_{50} \leq 10$ $\mu M$). Several of the compounds of the invention (IX, XXX, XXXI, XXXVIII, and XXXIX) are potent telomerase inhibitors, having approximate $IC_{50}$ values of less than, or equal to, about 5 $\mu M$.

With respect to the treatment of malignant diseases using the compounds described herein, compounds of the present invention are expected to induce crisis in telomerase-positive cell lines. Treatment of telomerase-positive cell lines, such as HEK-293 and HeLa cells, with a compound of the invention is also expected to induce a reduction of telomere length in the treated cells.

Compounds of the invention are also expected to induce telomere reduction during cell division in human tumor cell lines, such as the ovarian tumor cell lines OVCAR-5 and SK-OV-3. Importantly, however, in normal human cells used as a control, such as BJ cells of fibroblast origin, the observed reduction in telomere length is expected to be no different from cells treated with a control substance, e.g., dimethyl sulfoxide (DMSO). The compounds of the invention also are expected to demonstrate no significant cytotoxic effects at concentrations below about 5 $\mu M$ in the tumor cells.

In addition, the specificity of the compounds of the present invention for telomerase can be determined by comparing their activity ($IC_{50}$) with respect to telomerase to other enzymes having similar nucleic acid binding or modifying activity similar to telomerase in vitro. Such enzymes include DNA Polymerase I, HeLa RNA Polymerase II, T3 RNA Polymerase, MMLV Reverse Transcriptase, Topoisomerase I, Topoisomerase II, Terminal Transferase and Single-Stranded DNA Binding Protein (SSB). Compounds having lower $IC_{50}$ values for telomerase as compared to the $IC_{50}$ values toward the other enzymes being screened are said to possess specificity for telomerase.

In vivo testing can also be performed using a mouse xenograft model in which OVCAR-5 tumor cells are grafted onto nude mice. As discussed in Example B. 2 below, mice treated with a compound of the invention are expected to have tumor masses that, on average, may increase for a period following the initial dosing, but will begin to shrink in mass with continuing treatment. In contrast, mice treated with a control (e.g., DMSO) are expected to have tumor masses that continue to increase.

From the foregoing those skilled in the art will appreciate that the present invention also provides methods for selecting treatment regimens involving administration of a compound of the invention. For such purposes, it may be helpful to perform a TRF analysis in which DNA from tumor cells is analyzed by digestion with restriction enzymes specific for sequences other than the telomeric $(T_2AG_3)_N$ sequence. Following digestion of the DNA, gel electrophoresis is performed to separate the restriction fragments according to size. The separated fragments are then probed with nucleic acid probes specific for telomeric sequences to determine the lengths of the telomeres of the cells in the sample. By measuring the length of telomeric DNA, one can estimate how long a telomerase inhibitor should be administered and whether other methods of therapy (e.g., surgery, chemotherapy and/or radiation) should also be employed. In addition, during treatment, one can test cells to determine whether a decrease in telomere length over progressive cell divisions is occurring to demonstrate treatment efficacy.

V. Telomerase Inhibiting Compositions and Methods for Treating Diseases With the Same The present invention also provides pharmaceutical compositions for treating cancer and other conditions in which inhibition of telomerase is an effective therapy. These compositions include a therapeutically effective amount of a telomerase inhibiting compound of the invention in a pharmaceutically acceptable carrier or salt.

In one preferred embodiment, the present invention provides a composition effective for treating cancer in a mammal. The composition includes a therapeutically effective amount of a compound having the structure shown below (or a pharmaceutically acceptable salt thereof) in a pharmaceutically acceptable carrier.

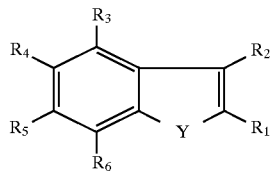

Y is selected from the group consisting of oxygen, sulfur, sulfonyl, sulfinyl, and $-NR_7-$. $R_1$ is $-TR_8$, where T is $-SO_2-$ or $-C(X_1)-$ and $R_8$ is selected from the group consisting of $-OR_9$, $-NHNHSO_2R_9$, $-NHNHC(X_2)OR_9$, $-NR_9R_{10}$, $-NHNHC(X_2)NR_9R_{10}$, $-NHCR_9R_{10}C(X_2)NR_{11}R_{12}$, $-NHC(X_2)NR_9R_{10}$, and the piperazinyl moiety shown below:

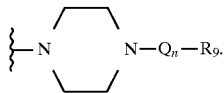

In the piperazinyl moiety shown above, n is 0 or 1, and $Q_n$, for n=1, is $-SO_2-$, $-C(X_2)-$ or $-C(X_2)NR_{10}-$. $R_2-R_6$ are selected independently from the group consisting of hydrogen, alkyl, aryl, hydroxyl, alkoxyl, aryloxyl, aralkoxyl, halogen, cyano, nitro, alkylcarbamido, arylcarbamido, dialkylcarbamido, diarylcarbamido, alkylarylcarbamido, alkylthiocarbamido, arylthiocarbamido, dialkylthiocarbamido, diarylthiocarbamido, alkylarylthiocarbamido, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, alkylcarbonyloxy, arylcarbonyloxy, carboxyl, alkoxycarbonyl, aryloxycarbonyl, sulfo, alkylsulfonylamido, arylsulfonamido, alkylsulfonyl, arylsulfonyl, alkylsulfinyl, and arylsulfinyl. $X_1$ and $X_2$ are selected independently from the group consisting of oxygen and sulfur. $R_7-R_{12}$ are selected independently from the group consisting of hydrogen, alkyl, aryl, aralkyl, heterocycle, and heterocyclealkyl.

In other preferred embodiments, the present invention provides a composition for treating cancer in a mammal comprising a therapeutically effective amount of a telomerase inhibitor of the invention having the structure shown above for Compound XLII or Compound XLIII (or pharmaceutically acceptable salts thereof) in a pharmaceutically acceptable carrier.

In addition, it will be appreciated that therapeutic benefits for treatment of cancer can be realized by combining a telomerase inhibitor of the invention with other anti-cancer agents, including other inhibitors of telomerase such as described in co-pending U.S. patent applications Ser. Nos. 08/535,988 (Attorney Docket No. GERNP004), entitled Telomerase Inhibitors, by inventors Federico C. A. Gaeta, and Elaine C. Stracker, filed Sep. 29, 1995; and Ser. No. 08/539,934 (Attorney Docket No. GERNP005), entitled Telomerase Inhibitors, by inventors Federico C. A. Gaeta, and Elaine C. Stracker, filed Oct. 6, 1995, both of which are incorporated herein by reference for every purpose. The choice of such combinations will depend on various factors including, but not limited to, the type of disease, the age and general health of the patient, the aggressiveness of disease progression, the TRF length and telomerase activity of the diseased cells to be treated and the ability of the patient to tolerate the agents that comprise the combination. For example, in cases where tumor progression has reached an advanced state, it may be advisable to combine a telomerase inhibiting compound of the invention with other agents and therapeutic regimens that are effective at reducing tumor size (e.g. radiation, surgery, chemotherapy and/or hormonal treatments). One regimen for reducing tumor size includes administration of a topoisomerase II-inhibitor, including those topoisomerase-II inhibitors described in the above-cited co-pending U.S. patent applications Ser. Nos. 08/535, 988 (Attorney Docket No. GERNP004) and Ser. No. 08/539, 934 (Attorney Docket No. GERNP005). In addition, in some cases it may be advisable to combine a telomerase inhibiting agent of the invention with one or more agents that treat the side effects of a disease, e.g., an analgesic, or agents effective to stimulate the patient's own immune response (e.g., colony stimulating factor).

In one such method, a pharmaceutical formulation comprises a telomerase inhibitor of the invention with an anti-angiogenesis agent, such as fumagillin, fumagillin derivatives, or AGM-1470. The latter compound is available from Takeda Chemical Industries, Ltd., while the former compounds are described in Ingber, et al., 6 Dec. 1990, "Synthetic analogues of fumagillin that inhibit angiogenesis and suppress tumor growth", *Nature* 348:555–557, incorporated herein by reference for all purposes. Other combinations may include, but are not limited to, a telomerase inhibitor of the invention in addition to one or more anti-neoplastic agents or adjuncts (e.g., folinic acid or mesna).

Antineoplastic agents suitable for combination with the compounds of the present invention include, but are not limited to, alkylating agents including alkyl sulfonates such as busulfan, improsulfan and piposulfan; aziridines, such as a benzodizepa, carboquone, meturedepa and uredepa; ethylenimines and methylmelamines such as altretamine, triethylenemelamine, triethylenephosphoramide, triethylenethiophosphoramide and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine and ranimustine. Additional agents include dacarbazine, mannomustine, mitobronitol, mitolactol and pipobroman. Still other classes of relevant agents include antibiotics, hormonal antineoplastics and antimetabolites. Yet other combinations will be apparent to those of skill in the art.

Additional agents suitable for combination with the compounds of the present invention include protein synthesis inhibitors such as abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, α-sarcin, shiga toxin, showdomycin, sparsomycin, spectinomycin, streptomycin, tetracycline, thiostrepton and trimethoprim. Inhibitors of DNA synthesis, including alkylating agents such as dimethyl sulfate, mitomycin C, nitrogen and sulfur mustards, MNNG and NMS; intercalating agents such as acridine dyes, actinomycins, adriamycin, anthracenes, benzopyrene, ethidium bromide, propidium diiodide-intertwining, and agents such as distamycin and netropsin, can also be combined with compounds of the present invention in pharmaceutical compositions. DNA base analogs such as acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, 5-fluorouracil, hydroxyurea and 6-mercaptopurine also can be used in combination therapies with the compounds of the invention. Topoisomerase inhibitors, such as coumermycin, nalidixic acid, novobiocin and oxolinic acid, inhibitors of cell division, including colcemide, colchicine, vinblastine and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin and streptolydigin also can be combined with the compounds of the invention to provide pharmaceutical compositions.

In another embodiment, the present invention includes compounds and compositions in which a telomerase inhibitor is either combined with or covalently bound to a cytotoxic agent bound to a targeting agent, such as a monoclonal antibody (e.g., a murine or humanized monoclonal antibody). It will be appreciated that the latter combination may allow the introduction of cytotoxic agents into cancer cells with greater specificity. Thus, the active form of the cytotoxic agent (i.e., the free form) will be present only in cells targeted by the antibody. Of course, the telomerase inhibitors of the invention may also be combined with monoclonal antibodies that have therapeutic activity against cancer.

In addition to the application of the telomerase inhibitors of the present invention to the treatment of mammalian diseases characterized by telomerase activity, telomerase inhibitors such as those disclosed herein, or in the above-cited co-pending U.S. patent applications Ser. Nos. 08/535,988 and 08/539,934 (Attorney Docket Nos. GERNP004 and GERNP005), can be applied to agricultural phytopathogenic organisms that are characterized by telomerase activity. These organisms include nematodes such as *Ceanorhabditis elegans*, in which telomerase activity has been found, and in fungi which are expected to have telomerase activity based on the determination that the DNA of the fungus *Ustilago maydis* exhibits telomeres having the tandem TTAGGG repeats that are maintained by telomerase. The telomerase-inhibiting compounds of the invention can be administered to plants and soil infected with phytopathogenic organisms having telomerase activity alone, or in combination with other telomerase-inhibiting agents (such as those in the above-cited U.S. patent applications Ser. Nos. 08/535,988 and 08/539,934 (Attorney Docket Nos. GERNP004 and GERNP005), or other telomerase inhibiting agents) and/or other agents used to control plant diseases. The determination of the compositions used to control such phytopathogenic organisms and the appropriate modes of delivering such compositions will be known to those having skill in the agricultural arts.

The determination that nematodes and possibly fungi have telomerase activity also indicates that the telomerase inhibitors provided by the present invention and the above-cited co-pending U.S. patent applications Ser. Nos. 08/535,988 and 08/539,934 (Attorney Docket Nos. GERNP004 and GERNP005) can be used to treat nematode infections in humans and animals of veterinary interest such as dogs and cats. Nematode infection in humans and animals often is in the form of hookworm or roundworm infection and leads to a host of deadly secondary illnesses such as meningitis, myocarditis, and various neurological diseases. Thus, it will be appreciated that administration of the telomerase-inhibiting compounds such as those of the invention or those described in the above-cited U.S. patent applications Ser. Nos. 08/535,988 and 08/539,934 (Attorney Docket Nos. GERNP004 and GERNP005), alone, or in combination with other telomerase-inhibiting agents and/or other therapeutic agents, can be used to control nematode and fungal infections in humans and animals.

In general, a suitable effective dose of a compound of the invention will be in the range of 0.001 to 1000 milligram (mg) per kilogram (kg) of body weight of the recipient per day, preferably in the range of 0.001 to 100 mg per kg of body weight per day, more preferably between about 0.1 and 100 mg per kg of body weight per day and still more preferably in the range of between 0.1 to 10 mg per kg of body weight per day. The desired dosage is preferably presented in one, two, three, four, or more subdoses administered at appropriate intervals throughout the day. These subdoses can be administered as unit dosage form, for example, containing 5 to 10,000 mg, preferably 10 to 1000 mg of active ingredient per unit dosage from. Preferably, the dosage is presented once per day at a dosing at least equal to TID.

The composition used in these therapies can be in a variety of forms. These include, for example, solid, semi-solid, and liquid dosage forms, such as tablets, pills, powders, liquid solutions or suspensions, liposomes, and injectable and infusible solutions. The preferred form depends on the intended mode of administration and therapeutic application. The compositions also preferably include conventional pharmaceutically acceptable carriers and adjuvants, as is well known to those of skill in the art. See, e.g., REMINGTON'S PHARMACEUTICAL SCIENCES, Mack Publishing Co.: Easton, Pa., 17th Ed. (1985). Preferably, administration will be by oral or parenteral (including subcutaneous, intramuscular, intravenous, and intradermal) routes. More preferably, the route of administration will be oral. The therapeutic methods and agents of this invention can of course be used concomitantly or in combination with other methods and agents for treating a particular disease or disease condition.

While it is possible to administer the active ingredient of this invention alone, it is preferable to present a therapeutic agent as part of a pharmaceutical formulation or composition. The formulations of the present invention comprise at least one telomerase activity-inhibiting compound of this invention in a therapeutically or pharmaceutically effective dose together with one or more pharmaceutically or therapeutically acceptable carriers and optionally other therapeutic ingredients. Various considerations for preparing such formulations are described, e.g., in Gilman et al. (eds.) GOODMAN AND GILMAN'S: *THE PHARMACOLOGICAL BASES OF THERAPEUTICS*, 8th Ed., Pergamon Press (1 990); and REMINGTON'S supra, each of which is incorporated herein by reference for all purposes. Methods for administration are discussed therein, e.g., for oral, intravenous, intraperitoneal, intramuscular, and other forms of administration. Typically, methods for administering pharmaceutical compositions will be either topical, parenteral, or oral administration methods for prophylactic and/or therapeutic treatment. Oral administration is preferred. The pharmaceutical compositions can be administered in a variety of unit dosage forms depending upon the method of administration. As noted above, unit dosage forms suitable for oral administration include powders, tablets, pills, and capsules.

One can use topical administration to deliver a compound of the invention by percutaneous passage of the drug into the systemic circulation of the patient. The skin sites include anatomic regions for transdermally administering the drug, such as the forearm, abdomen, chest, back, buttock, and mastoidal area. The compound is administered to the skin by placing on the skin either a topical formulation comprising the compound or a transdermal drug delivery device that administers the compound. In either embodiment, the delivery vehicle is designed, shaped, sized, and adapted for easy placement and comfortable retention on the skin.

A variety of transdermal drug delivery devices can be employed with the compounds of this invention. For example, a simple adhesive patch comprising a backing material and an acrylate adhesive can be prepared. The drug and any penetration enhancer can be formulated into the adhesive casting solution. The adhesive casting solution can be cast directly onto the backing material or can be applied to the skin to form an adherent coating. See, e.g., U.S. Pat. Nos. 4,310,509; 4,560,555; and 4,542,012.

In other embodiments, the compound of the invention will be delivered using a liquid reservoir system drug delivery device. These systems typically comprise a backing material, a membrane, an acrylate based adhesive, and a release liner. The membrane is sealed to the backing to form a reservoir. The drug or compound and any vehicles, enhancers, stabilizers, gelling agents, and the like are then incorporated into the reservoir. See, e.g., U.S. Pat. Nos. 4,597,961; 4,485,097; 4,608,249; 4,505,891; 3,843,480; 3,948,254; 3,948,262; 3,053,255; and 3,993,073.

Matrix patches comprising a backing, a drug/penetration enhancer matrix, a membrane, and an adhesive can also be employed to deliver a compound of the invention transdermally. The matrix material typically will comprise a polyurethane foam. The drug, any enhancers, vehicles, stabilizers, and the like are combined with the foam precursors. The foam is allowed to cure to produce a tacky, elastomeric matrix which can be directly affixed to the backing material. See, e.g., U.S. Pat. Nos. 4,542,013; 4,460,562; 4,466,953; 4,482,534; and 4,533,540.

Also included within the invention are preparations for topical application to the skin comprising a compound of the invention, typically in concentrations in the range from about 0.001% to 10%, together with a non-toxic, pharmaceutically acceptable topical carrier. These topical preparations can be prepared by combining an active ingredient according to this invention with conventional pharmaceutical diluents and carriers commonly used in topical dry, liquid, and cream formulations. Ointment and creams may, for example, be formulated with an aqueous or oily base with the addition of suitable thickening and/or gelling agents. Such bases may include water and/or an oil, such as liquid paraffin or a vegetable oil, such as peanut oil or castor oil. Thickening agents that may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like. Topical administration of compounds of the invention may also be preferred for treating diseases such as skin cancer and fungal infections of the skin (pathogenic fungi typically express telomerase activity).

The topical pharmaceutical compositions according to this invention may also include one or more preservatives or bacteriostatic agents, e.g., methyl hydroxybenzoate, propyl hydroxybenzoate, chlorocreosol, benzalkonium chlorides, and the like. The topical pharmaceutical compositions also can contain other active ingredients such as antimicrobial agents, particularly antibiotics, anesthetics, analgesics, and antipruritic agents.

The compounds of the present invention can also be delivered through mucosal membranes. Transmucosal (i.e., sublingual, buccal, and vaginal) drug delivery provides for an efficient entry of active substances to systemic circulation and reduces immediate metabolism by the liver and intestinal wall flora. Transmucosal drug dosage forms (e.g., tablet, suppository, ointment, pessary, membrane, and powder) are typically held in contact with the mucosal membrane and disintegrate and/or dissolve rapidly to allow immediate systemic absorption. Note that certain such routes may be used even where the patient is unable to ingest a treatment composition orally. Note also that where delivery of a telomerase inhibitor of the invention would be enhanced, one can select a composition for delivery to a mucosal membrane, e.g., in cases of colon cancer one can use a suppository to deliver the telomerase inhibitor.

For delivery to the buccal or sublingual membranes, typically an oral formulation, such as a lozenge, tablet, or capsule, will be used. The method of manufacture of these formulations is known in the art, including, but not limited to, the addition of the pharmacological agent to a pre-manufactured tablet; cold compression of an inert filler, a binder, and either a pharmacological agent or a substance containing the agent (as described in U.S. Pat. No. 4,806, 356); and encapsulation. Another oral formulation is one that can be applied with an adhesive, such as the cellulose derivative hydroxypropyl cellulose, to the oral mucosa, for example as described in U.S. Pat. No. 4,940,587. This buccal adhesive formulation, when applied to the buccal mucosa, allows for controlled release of the pharmacological agent into the mouth and through the buccal mucosa.

Parenteral administration is generally characterized by injection, either subcutaneously, intramuscularly, or intravenously. Thus, this invention provides compositions for intravenous administration that comprise a solution of a compound of the invention dissolved or suspended in an acceptable carrier. Injectables can be prepared in conventional forms, either as liquid solutions or suspensions, solid forms suitable for solution or suspension in liquid prior to injection, or as emulsions. Suitable excipients are, for example, water, buffered water, saline, dextrose, glycerol, ethanol, or the like. These compositions will be sterilized by conventional, well known sterilization techniques, such as sterile filtration. The resulting solutions can be packaged for use as is or lyophilized, the lyophilized preparation being combined with a sterile solution prior to administration. In addition, if desired, the pharmaceutical compositions to be administered may also contain minor amounts of non-toxic auxiliary substances, such as wetting or emulsifying agents, pH buffering agents and the like, such as for example, sodium acetate, sorbitan monolaurate, triethanolamine oleate, etc. Such formulations will be useful in treating ovarian cancers.

Another method of parenteral administration employs the implantation of a slow-release or sustained-release system, such that a constant level of dosage is maintained. See, e.g., U.S. Pat. No. 3,710,795, incorporated herein by reference.

Liquid pharmaceutically administrable compositions can, for example, be prepared by dissolving, dispersing, etc., an active compound as defined above and optional pharmaceutical adjuvants in an excipient, such as, for example, water, saline, aqueous dextrose, glycerol, ethanol, olive oil, and other lipophilic solvents, and the like, to form a solution or suspension. If desired, the pharmaceutical composition to be administered may also contain minor amounts of nontoxic auxiliary substances, such as wetting or emulsifying agents, pH buffering agents, and the like, for example, sodium acetate, sorbitan monolaurate, triethanolamine sodium acetate, triethanolamine oleate, etc. Actual methods of preparing such dosage forms are known and will be apparent to those skilled in this art; for example, see REMINGTON'S PHARMACEUTICAL SCIENCES, supra. The composition or formulation to be administered will contain an effective amount of an active compound of the invention.

For solid compositions, conventional nontoxic solid carriers can be used and include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.1–95% of active ingredient, preferably about 20%.

The compositions containing the compounds of the invention can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective amount or dose." Amounts effective for this use will depend on the severity of the disease and the weight and general state of the patient.

In addition to internal (in vivo) administration, the compounds and compositions of the invention may be applied ex vivo to achieve therapeutic effects, as for example, in the case of a patient suffering from leukemia. In such an application, cells to be treated, e.g., blood or bone marrow cells, are removed from a patient and treated with a pharmaceutically effective amount of a compound of the invention. The cells are returned to the patient following treatment. Such a procedure can allow for exposure of cells to concentrations of therapeutic agent for longer periods or at higher concentrations than otherwise available.

Once improvement of the patient's conditions has occurred, as, for example, by the occurrence of remission in the case of a cancer patient, a maintenance dose is administered if necessary. Subsequently, the dosage or the frequency of administration, or both, can be reduced, as a function of the systems, to a level at which the improved condition is retained. When the symptoms have been alleviated to the desired level, treatment can cease. Patients can, however, require additional treatment upon any recurrence of the disease symptoms.

In prophylactic applications (e.g. chemoprevention), compositions containing the compounds of the invention are administered to a patient susceptible to or otherwise at risk of a particular disease. Such an amount is defined to be a "prophylactically effective amount or dose." In this use, the precise amounts again depend on the patient's state of health and weight.

As will be apparent to those of skill in the art upon reading of this disclosure, the present invention provides valuable reagents relating to human telomerase. The above description of necessity provides a limited and merely illustrative sampling of specific compounds, and should not be construed as limiting the scope of the invention. Other features and advantages of the invention will be apparent from the following examples and claims.

EXAMPLES

The following examples describe specific aspects of the invention to illustrate the invention and also provide a description of methods that can be used to identify and test compounds that inhibit the activity of telomerase to aid those of skill in the art in understanding and practicing the invention. The examples should not be construed as limiting the invention in any manner.

A. Chemical Syntheses

The following procedures illustrate the syntheses of compounds in the class defined by the structure of Compound I.

General Procedure for the Preparation of Cinnamic Acids

A 500 milliter (ml) round-bottomed flask, Teflon stirrer, reflux condenser, and gas inlet were oven-dried for 12 hours at 160° C. The apparatus was rapidly assembled, flushed with dry nitrogen gas, and allowed to cool to room temperature. After cooling, the flask was charged with malonic acid (220 mmole), pyridine (150 ml), aromatic aldehyde (200 mmole) and piperidine (4 ml, 40 mmole). The reaction mixture was stirred as it was heated to reflux. After 16 hours of heating and stirring, the reaction mixture was cooled to room temperature and poured onto a mixture of ice (200 ml) and concentrated hydrochloric acid (200 ml) resulting in the precipitation of a white solid to form a slurry. The slurry was stirred for 2 hours, filtered, washed with cold water (2×500 ml) and dried in vacuo to give the desired cinnamic acid in good to excellent yield (75–90%).

Preparation of 2,3-Dichlorocinnamic Acid

A 250 ml round-bottomed flask, Teflon stirrer, reflux condenser, and gas inlet were oven-dried for 12 hours at 160° C. The apparatus was rapidly assembled, flushed with dry nitrogen gas, and allowed to cool to room temperature. After cooling, the flask was charged with malonic acid (110 mmole), pyridine (75 ml), 2,3-dichlorobenzaldehyde (17.50 g, 100 mmole) and piperidine (2 ml, 20 mmole). The reaction mixture was stirred and brought to relux. After 16 hours of stirring under reflux, the reaction mixture was cooled to room temperature and poured onto a mixture of ice (100 ml) and concentrated hydrochloric acid (100 ml) resulting in the precipitation of a white solid to form a slurry. The resulting slurry was stirred for 2 hours, filtered, washed with cold water (2×250 ml), and dried in vacuo to give 20.01 g (92%) of 2,3-dichlorocinnamic acid.

Synthesis of 6-Methoxy-3—Chlorobenzo[b]thiophene-2-Carbonyl Chloride

A 100 milliliter (ml) 3-necked, round-bottomed flask, reflux condenser, thermometer adapter, gas inlet and Teflon stirrer were oven dried for 12 hours at 160° C. The apparatus was rapidly assembled, fitted with a thermometer, flushed with dry nitrogen gas, sealed with rubber septa and allowed to cool to room temperature. The reaction flask was then charged with 4-methoxycinnamic acid (Aldrich, 10 g, 60 mmole), anhydrous pyridine (Aldrich, 1 ml, 12.4 mmole), anhydrous dimethylformamide (Aldrich 2.0 ml, 25.8 mmole) and anhydrous chlorobenzene (Aldrich, 10 ml) at room temperature. At this point the apparatus was disconnected from the dry nitrogen source.

Thionyl chloride (Aldrich, 205.6 mmole, 15 ml) was added to the reaction mixture in a dropwise fashion over a period of 10 minutes using a syringe. Evolution of hydrogen chloride was observed together with the rapid dissolution of the white solid in the flask to give a yellow-brown solution. Upon completion of the addition, the reaction mixture was stirred rapidly at room temperature for 30 minutes and then heated by means of a heating mantle to 140°–145° C. for 5 hours. Upon cooling the reaction mixture to room temperature, the dark brown solution solidified.

The contents of the flask were broken into small pieces, slurried and transferred to a 1000 ml Erlenmeyer flask using hot, dry hexane (500 ml, dried over magnesium sulfate, 25 g/1000 ml). The hot hexane slurry was heated to boiling for 30 minutes during which time most of the residue gradually dissolved. The resulting orange-yellow hot hexane solution was decanted from the remaining residue and concentrated to 350 ml. The solution was allowed to cool to room temperature, and was stored at 4 C. overnight. During this period a yellow precipitate formed. The precipitate was filtered off and dried in vacuo to give 4.00 g of the desired material. Further concentration of the filtrate to 200 ml and repeating the above mentioned crystallization steps yielded an additional 1.00 g. $^1$H NMR (in dimethylsulfoxide-d$_6$ (DMSO-d$_6$) at 400 megahertz (MHz)) indicated that both samples were contaminated with 4-methoxy cinnamoyl chloride. Pure material could be produced by recrystallization from dry hexane.

Synthesis of 6-Methyl-3—Chlorobenzo[b]thiophene-2—Carbonyl Chloride

A 250 ml, 3-necked, round bottomed flask, reflux condenser, thermometer adapter, gas inlet and Teflon stirrer were oven dried for 12 hours at 160° C. The apparatus was rapidly assembled, fitted with a thermometer, flushed with dry nitrogen gas, sealed with rubber septa and allowed to cool to room temperature. The reaction flask was charged with 4-methylcinnamic acid (Aldrich, 20 g, 123.31 mmole), anhydrous pyridine (Aldrich, 2.2 ml, 27.28 mmole), anhydrous dimethylformamide (Aldrich, 4.4 ml, 56.82 mmole) and anhydrous chlorobenzene (Aldrich, 20 ml) at room temperature. At this point the apparatus was disconnected from the dry nitrogen source.

Thionyl chloride (Aldrich, 451.32 mmole, 39.1 ml) was added to the reaction mixture in a dropwise fashion by means of a syringe, over a period of 20 minutes. Evolution of hydrogen chloride was observed, together with the rapid dissolution of the white solid in the flask to give a yellow-brown solution. Upon completion of addition, the reaction mixture was rapidly stirred at room temperature for 30 minutes and then heated by means of a heating mantle to reflux for 16 hours. Upon cooling the reaction mixture to room temperature, the dark brown solution solidified.

The contents of the flask were broken into small pieces, slurried and transferred to a 2000 ml Erlenmeyer flask using hot, dry hexane (1000 ml, dried over magnesium sulfate, 25 g/1000 ml). The hot hexane slurry was heated to boiling for 30 minutes during which time, most of the residue gradually dissolved. The resulting orange-yellow hot hexane solution was decanted off from the remaining residue and concentrated to 750 ml. The solution was allowed to cool to room temperature, and then stored at 4° C. overnight. This resulted in a yellow precipitate, which was filtered off and dried in vacuo, to give 19.46 g of the desired material. 'H NMR (DMSO-d$_6$, 400 MHz) indicated that the recovered material was predominantly the desired material (a purity of greater than 95% was determined by NMR).

Preparation of 6-Methoxy-7,3-Dichlorobenzo[b]thiophene-2-Carbonyl Chloride

A 100 ml, 3-necked, round bottomed flask, reflux condenser, thermometer adapter, gas inlet and Teflon stirrer were oven dried for 12 hours at 160° C. The apparatus was rapidly assembled, fitted with a thermometer, flushed with dry nitrogen gas, sealed with rubber septa and cooled to room temperature. The reaction flask was charged with 4-methoxycinnamic acid (Aldrich, 10 g, 60 mmole), anhydrous pyridine (Aldrich, 1 ml, 12.4 mmole), anhydrous dimethylformamide (Aldrich, 2.0 ml, 25.8 mmole) and anhydrous chlorobenzene (Aldrich, 10 ml) at room temperature. At this point the apparatus was disconnected from the dry nitrogen source.

Thionyl chloride (Aldrich, 205.6 mmole, 15 ml) was added to the reaction mixture in a dropwise fashion by means of a syringe, over a period of 10 minutes. Evolution of hydrogen chloride was observed, together with the rapid dissolution of the white solid in the flask to give a yellow-brown solution. Upon completion of addition, the reaction mixture was rapidly stirred at room temperature for 30 minutes and then the mixture was heated by means of a heating mantle to a temperature of 140°–145° C. for 6 days. Upon cooling the reaction mixture to room temperature, the dark brown solution solidified.

The contents of the flask were broken into small pieces, slurried and transferred to a 1000 ml Erlenmeyer flask using hot, dry hexane (500 ml, dried over magnesium sulfate, 25 g/ 1000 ml). The hot hexane slurry was heated to boiling for 30 minutes during which time, most of the residue gradually dissolved. The resulting orange-yellow hot hexane solution was decanted from the remaining residue and the solution was concentrated to 350 ml. The solution was cooled to room temperature, and then stored at 4° C. overnight. A yellow precipitate formed during the cooling, which was filtered off, and dried in vacuo, to give 2.25 g of the desired material. Further concentration of the filtrate to 200 ml and repeating the above described crystallization steps yielded an additional 1.20 g.

Preparation of 6-Methoxy-7-Chlorobenzo[b]thiophene-2-Carbonyl Chloride

A 100 ml, 3-necked, round bottomed flask, reflux condenser, thermometer adapter, gas inlet and Teflon stirrer were oven dried for 12 hours at 160° C. The apparatus was rapidly assembled, fitted with a thermometer, flushed with dry nitrogen gas, sealed with rubber septa and cooled to room temperature. The reaction flask was charged with 4-methoxycinnamic acid (Aldrich, 10 g, 60 mmole), anhydrous pyridine (Aldrich, 1 ml, 12.4 mmole), anhydrous dimethylformamide (Aldrich, 2.0 ml, 25.8 mmole) and anhydrous chlorobenzene (Aldrich, 100 ml) at room temperature. At this point the apparatus was disconnected from the dry nitrogen source.

Thionyl chloride (Aldrich, 480 mmole, 35 ml) was added to the reaction mixture in a dropwise fashion by means of a syringe, over a period of 10 minutes. Evolution of hydrogen chloride was observed, together with the rapid dissolution of the white solid in the flask to give a yellow-brown solution. Upon completion of addition, the reaction mixture was rapidly stirred at room temperature for 30 minutes and then heated by means of a heating mantle to a temperature of 140°–145° C. for 6 days. Upon allowing the reaction mixture to cool to room temperature, the dark brown solution solidified.

The excess thionyl chloride and chlorobenzene was removed by distillation at reduced pressure. Upon completion of the distillation, the contents of the flask were broken-up into small pieces, slurried and transferred to a 1000 ml Erlenmeyer flask using hot, dry hexane (500 ml, dried over magnesium sulfate, 25 g/1000 ml). The hot hexane slurry was heated to boiling for 30 minutes during which time, most of the residue gradually dissolved. The resulting orange-yellow hot hexane solution was decanted from the remaining residue and concentrated to 350 ml. The solution was cooled to room temperature, and then stored at 4° C. overnight. A yellow precipitate formed which was filtered off, and dried in vacuo, to give 1.25 g of the 7-chloro[b] benzothiophene.

General Preparation of Methyl, Ethyl and Isopropyl Esters from Aryl or Heteroaryl Acyl Chlorides The corresponding carboxylic acid (10 mmoles) was transferred to a 100 ml round bottomed flask. Anhydrous methanol (Aldrich, 50 ml) was added and the acid dissolved by stirring. To this stirred solution was added chlorotrimethylsilane ($Si(CH_3)_3Cl$, 2.5 equivalents, 25 mmole). The reaction mixture was stirred at room temperature and monitored by TLC (silica, 1:1 hexane:ethyl acetate, iodine stain and UV visualization). Upon completion of the reaction as determined by TLC analysis (16–48 hours at room temperature), the resulting solution was concentrated in vacuo to give crude material, which was shown by $^1$H NMR (DMSO-$d_6$, 400 MHz) to be the desired material in a high level of purity. The crude methyl ester can be used directly or recrystallized from a suitable solvent (e.g., methanol, ethanol or acetonitrile).

The preparation of the corresponding ethyl and isopropyl esters was accomplished using the same technique, but ethanol or isopropyl alcohol was substituted for methanol respectively.

Preparation of Methyl 6-Methoxy-3-Chlorobenzo[b]thiophene-2-Carboxylate

Crude 6-methoxy-3-chlorobenzo[b]thiophene-2-carbonyl chloride (2 g, 7.67 mmoles) was transferred to a 100 ml round bottomed flask. Anhydrous methanol (Aldrich, 50 ml) was added and the acid chloride dissolved by stirring. To this stirred solution was added chlorotrimethylsilane (2.5 equivalents, 19.16 mmole, 2.08 g, 2.43 ml). The reaction mixture was stirred overnight at room temperature. TLC analysis (silica, 1:1 hexane:ethyl acetate, UV visualization) indicated complete conversion of the acid chloride to the methyl ester. The resulting slurry was concentrated in vacuo to give a yellow solid, which was shown by $^1$H NMR (DMSO-$d_6$, 400 MHz) to be the desired material. The crude methyl ester was dissolved in hot ethanol (200 ml), the volume was reduced to 150 ml, and allowed to cool to room temperature. The resulting orange ethanolic solution was cooled to −10° C. for 15 minutes. The resulting precipitate was filtered off and dried in vacuo to give 1.25 g of the ester as an off-white solid.

Preparation of Methyl 6-Methyl-3-Chlorobenzo[b]thiophene-2-Carboxylate

Crude 6-methyl-3-chlorobenzo[b]thiophene-2-carbonyl chloride (5 g, 20.46 mmoles) was transferred to a 250 ml round bottomed flask. Anhydrous methanol (Aldrich, 80 ml) was added and the acid chloride dissolved by stirring. To this stirred solution was added chlorotrimethylsilane (3.0 equivalents, 61.38 mmole, 6.68 g, 7.80 ml). The reaction mixture was stirred at room temperature and the progress of the reaction monitored by TLC (silica, 1:1 hexane:ethyl acetate, iodine and UV visualization). The reaction was shown to be complete after 24 hours. The resulting slurry was concentrated in vacuo to give 4.80 g of a yellow solid, which was shown by $^1$H NMR (DMSO-$d_6$, 400 MHz) to be the desired material. The crude methyl ester was shown to be pure and used directly.

General Method for the Preparation of Aryl and Heteroaryl Hydrazides from Aryl and Heteroaryl Esters A 100 ml bottomed flask, reflux condenser, gas inlet and Teflon stirrer were oven dried for 12 hours at 160° C. The apparatus was rapidly assembled, flushed with dry nitrogen gas, and allowed to cool to room temperature. The reaction flask was charged with methyl ester (5.0 mmole), anhydrous methanol (Aldrich, 50 ml), and anhydrous hydrazine (Aldrich, 2.5 equivalents, 12.5 mmole). The stirred reaction mixture was brought to reflux and the progress of the reaction monitored by TLC (silica, 1:1 hexane:ethyl acetate, iodine and UV visualization). Upon completion of the reaction, the reaction mixture was cooled to room temperature, and further cooled to 5° C. for 1 hour. The resulting solid was filtered off, washed with cold methanol (2×10 ml), and dried in vacuo. The resulting hydrazide was sufficiently pure to be used directly.

General Method for the Preparation of Aryl and Heteroaryl Hydrazides from Aryl and Heteroaryl Acyl or Sulfonyl Chlorides A 250 ml, 3-necked round bottomed flask, Teflon stirrer, 50 ml pressure equalized addition funnel, and gas inlet were oven dried for 12 hours at 160 ° C. The apparatus was rapidly assembled, flushed with dry nitrogen gas, and cooled to room temperature. The reaction flask was charged with anhydrous THF (Aldrich, 100 ml) and anhydrous hydrazine (Aldrich, 131.0 mmole, 4.21 g, 4.12 ml). The reaction mixture was cooled to 0° C. (ice/water), and a THF solution (20 ml) of 2-naphthoyl chloride (10 g, 52.54 moles) was added over 30 minutes in a dropwise fashion to the stirred reaction mixture. Upon completion of addition, the reaction mixture was warmed to room temperature and stirred overnight. The reaction mixture was poured onto ice/water (1000 ml), and vigorously stirred for 1 hour. The resulting white slurry was filtered, washed with cold water (4×50 ml), and dried in vacuo to give 9.80 g of a white powder. $^1$H NMR (DMSO-d$_6$, 400 MHz) showed the product to be pure.

Preparation of 6-Methoxy-3-Chlorobenzo[b]thiophene-2-Hydrazide

A 100 ml, round bottomed flask, reflux condenser, gas inlet and Teflon stirrer were oven dried for 12 hours at 160° C. The apparatus was rapidly assembled, flushed with dry nitrogen gas, and cooled to room temperature. The reaction flask was charged with methyl 6-methoxy-3-chlorobenzo[b]thiophene-2-carboxylate (1.50 g, 5.85 mmole), anhydrous methanol (Aldrich, 50 ml), and anhydrous hydrazine (Aldrich, 2.5 equivalents, 0.47 g, 0.45 ml, 14.61 mmole). The stirred reaction mixture was brought to reflux and the progress of the reaction monitored by TLC (Silica, 1:1 hexane:ethyl acetate, iodine and UV visualization). After 72 hours, the completed reaction was cooled to room temperature, and further cooled to 5° C. for 1 hour. The resulting solid was filtered, washed with cold methanol (2×10 ml), and dried in vacuo. This resulted in 0.856 g of the desired material, as a white amorphous powder which was used directly.

Preparation of 3-Chlorobenzo[b]thiophene-2-Carboxy-2'-[(2,5-Dichlorophenylamino)thia]hydrazine A 50 ml round bottomed flask, Teflon stirrer and gas inlet were oven dried for 12 hours at 160° C. The apparatus was flushed with dry nitrogen and cooled. The reaction flask was charged with 3-chlorobenzo[b]thiophene-2-carboxyhydrazide (2 g, 8.85 mmole), which was dissolved with anhydrous tetrahydrofuran (THF, 25 ml). To this homogeneous reaction mixture was added 2,5-dichlorophenyl isothiocyanate (1.88 g, 9.2 mmole) in anhydrous THF (4 ml). The reaction mixture was stirred at room temperature for 24 hours. The resulting slurry was diluted with anhydrous THF (10 ml), and stirred for a further 10 minutes. The solid was filtered off, washed with 1:1 hexane-diethyl ether (15 ml), and dried in vacuo to give 1.21 g of pure product.

Preparation of 3-Chlorobenzo[b]thiophene-2-Carboxy-2'-[(3,4-Dichlorophenylamino)oxa]hydrazine A 50 ml round bottomed flask, Teflon stirrer and gas inlet were oven dried for 12 hours at 160° C. The apparatus was flushed with dry nitrogen and cooled. The reaction flask was charged with 3-chlorobenzo[b]thiophene-2-carboxyhydrazide (2 g, 8.85 mmole), which was dissolved with anhydrous THF (25 ml). 3,4-Dichlorophenyl isocyanate (1.73 g, 9.2 mmole) in anhydrous THF (4 ml) was added in one lot to the stirred homogeneous reaction mixture. The reaction mixture was stirred at room temperature for 24 hours. The resulting slurry was diluted with anhydrous THF (10 ml), and stirred for a further 10 minutes. The solid was filtered, washed with 1:1 hexane-diethyl ether (15 ml), and dried in vacuo to give 1.21 g of pure product.

Preparation of Methyl 4-Chlorobenzo[b]thiophene-2-Carboxylate

A 100 ml 3-necked round-bottomed flask, reflux condenser, thermometer adapter, gas inlet, and Teflon stirrer were oven-dried for 12 hours at 160° C. The apparatus was rapidly assembled, fitted with a thermometer, flushed with dry nitrogen gas, sealed with rubber septa, and allowed to cool to room temperature. The cooled reaction flask was charged with anhydrous dimethyl sulfoxide (40 ml), 2-fluoro-6-chlorobenzaldehyde (5 g, 31.53 mmole), anhydrous triethylamine (2.5 equivalents, 78.83 mmole, 7.976 g, 11 ml) and methyl thioglycolate (1.1 equivalents, 3.681 g, 3.10 ml, 34.68 mmole). The reaction mixture was heated to 75° C. with rapid stirring. The progress of the reaction was monitored by thin-layer chromatography (TLC, silica, 10% dichloromethane-hexane developing solution and UV visualization). After 3 hours the reaction mixture was allowed to cool to room temperature and poured into an ice/water mixture (250 ml). The resulting slurry was stirred for 20 minutes, filtered, washed with cold water (2×100 ml) and dried in vacuo to give 6.07 g (85%) of methyl 4-chlorobenzo[b]thiophene-2-carboxylate. See, A. J. Bridges, A. Lee, E. C. Madukor, and C. E. Schwartz, *Tetrahedron Letters*, 33:7499 (1992).

Preparation of Methyl 4-fluorobenzo[b]thiophene-2-Carboxylate

A 100 ml 3-necked round-bottomed flask, reflux condenser, thermometer adapter, gas inlet, and Teflon stirrer were oven-dried for 12 hours at 160° C. The apparatus was rapidly assembled, fitted with a thermometer, flushed with dry nitrogen gas, sealed with rubber septa, and allowed to cool to room temperature. The cooled reaction flask was charged with anhydrous dimethyl sulfoxide (40 ml), 2,6-difluorobenzaldehyde (5 g, 35.18 mmole), anhydrous triethylamine (2.5 equivalents, 87.95 mmole, 8,952 g, 12.33 ml) and methyl thioglycolate (1.1 equivalents, 4.10 g, 38.70 mmole). The mixture was heated to 75° C. with rapid stirring. The progress of the reaction was monitored by TLC (silica, 10% dichloromethane-hexane, UV visualization). After 19 hours the reaction mixture was cooled to room temperature and poured onto an ice/water mixture (250 ml). The resulting slurry was stirred for 20 minutes, filtered, washed with cold water (2×100 ml) and dried in vacuo to give 5.76 g (78%) of methyl 4-fluorobenzo[b]thiophene-2-carboxylate. See, A. J. Bridges, A. Lee, E. C. Madukor, and C. E. Schwartz, *Tetrahedron Letters*, 33:7499 (1992).

Preparation of Methyl benzo[b]thiophene-2-Carboxylate

A 100 ml 3-necked round-bottomed flask, reflux condenser, thermometer adapter, gas inlet, and Teflon stirrer were oven-dried for 12 hours at 160° C. The apparatus was rapidly assembled, fitted with a thermometer, flushed with dry nitrogen gas, sealed with rubber septa and allowed to cool to room temperature. The cooled reaction flask was charged with anhydrous dimethyl sulfoxide (40 ml), 2-fluorobenzaldehyde (4.44 g, 31.53 mmole), anhydrous triethylamine (2.5 equivalents, 78.83 mmole, 7.976 g, 11 ml) and methyl thioglycolate (1.1 equivalents, 3.681 g, 3.10 ml, 34.68 mmole) and heated to 75° C. with rapid stirring. The progress of the reaction was monitored by TLC (silica, 10% dichloromethane-hexane, UV visualization). After 18 hours the reaction mixture was cooled to room temperature and poured onto an ice/water bath (250 ml). The resulting slurry was stirred for 20 minutes, filtered, washed with cold water (2×100 ml) and dried in vacuo to give 5.136 g (85%) of methyl benzo[b]thiophene-2-carboxylate.

Preparation of Methyl 5-Nitrobenzo[b]thiophene-2-Carboxylate

A 2000 ml 3-necked round-bottomed flask, 250 ml pressure equalized dropping funnel, Teflon stirrer, and gas inlet were oven-dried for 12 hours at 160° C. The apparatus was rapidly assembled, fitted with a thermometer, flushed with dry nitrogen gas, and allowed to cool to room temperature. The cooled flask was charged with methanol (600 ml) and methyl thioglycolate (28.6 g, 0.27 mole). Sodium methoxide (19,98 g, 0.37 mole) in methanol (125 ml) was added to the reaction mixture over 10 minutes while stirring. The reaction mixture was then warmed to 40° C. and a solution of 2-chloro-5-nitrobenzaldehyde (28.6 g, 0.27 mole) in methanol (300 ml) was added over a period of about 20 minutes. The resulting slurry was stirred at 40° C. for 1 hour, cooled to room temperature, and acidified with 2M hydrochloric acid. The resulting white solid was filtered, washed with water (2×300 ml) and air-dried to give 61 g (95%) of methyl 5-nitrobenzothiophene-2-carboxylate. See, R. A. Zambias, M. L. Hammond, *Synthetic Communications*, 21:959 (1991).

Preparation of Methyl 5-aminobenzo[b]thiophene-2-Carboxylate

In a 250 ml round-bottomed flask fitted with a Teflon stirrer and a reflux condenser, methyl 5-nitrobenzo[b]thiophene-2-carboxylate (10 g, 42.18 mmole) was dissolved in ethanol (100 ml). Tin (II) chloride dihydrate (5 equivalents, 47.60 g, 211 mmole) was added in one lot and the resulting slurry was reluxed for 18 hours while being stirred. The reaction mixture was cooled to room temperature, transferred to a 2000 ml Erlenmeyer flask, and carefully quenched with 5% sodium bicarbonate solution (aprroximately 700 ml) until effervescense was no longer detected. The resulting precipitate was filtered off and air-dried. The dried solid was dissolved in hot ethanol (500 ml), and filtered to remove undissolved material. The filtrate was evaporated in vacuo to give 8.564 g (96%) of methyl 5-aminobenzo[b]thiophene-2-carboxylate.

B. Anti-tumor Activity

1. Ex vivo Studies a. Reduction of Telomere Length in Tumor Cells

Colonies of the tumor cell lines, such as the ovarian tumor cell lines OVCAR-5 and SK-OV-3, and normal human cells used as a control (e.g., normal human BJ cells) are prepared using standard methods and materials. In one test, the colonies are prepared by seeding 15-centimeter dishes with about $10^6$ cells in each dish. The dishes are incubated to allow the cell colonies to grow to about 80% confluence, at which time each of the colonies are divided into two groups. One group is exposed to a subacute dose of a compound of the invention at a predetermined concentration (e.g., between about 5 $\mu$M and about 20 $\mu$M) for a period of about 4–8 hours after plating following the split; the other group is exposed to a control (e.g., DMSO).

Each group is then allowed to continue to divide, and the groups are split evenly again (near confluence). The same number of cells are seeded for continued growth. The compound or control is added every fourth day to the samples at the same concentration delivered initially. Remaining cells are analyzed for telomere length. As the untested cell cultures near confluence, the samples are split again as just described. This sequence of cell doubling and splitting is continued for about 20 to 25 doublings. Thus, a determination of telomere length as a function of cell doublings is obtained.

Telomere length is determined by digesting the DNA of the cells using restriction enzymes specific for sequences other than the repetitive $T_2AG_3$ sequence of human telomeres. The digested DNA is separated by size using standard techniques of gel electrophoresis to determine the lengths of the telomeric repeats, which appear, after probing, on the gel as a smear of high-molecular weight DNA (approximately 2 Kb–15 Kb).

The results of the telomere length analysis are expected to indicate that the compounds of the invention have no affect on the rate of decrease in telomere length for control cells as a function of progressive cell doublings. With respect to the tumor cell lines, however, measurable decreases in telomere length are expected to be determined for tumor cells exposed to the compounds of the invention. Tumor cells exposed to the control are expected to maintain steady telomere lengths. Thus, the compounds of the invention are expected to cause resumption of the normal loss of telomere length as a function of cell division in tumor cells.

In another experiment, HEK-293 cells are incubated with a compound of the invention and a control at concentrations between about 1 $\mu$M and about 20 $\mu$M using the protocol just described. Cells are expected to enter crisis (i.e., the cessation of cell function) within several weeks following administration of the test compound of the invention. In addition, TRF analysis of the cells using standard methodology is expected to show that the test compounds of the invention are effective in reducing telomere length. In addition to the HEK-293 cells described above, this assay can be performed with any telomerase-positive cell line, such as HeLa cells.

b. Specificity

Compounds of the invention are screened for activity ($IC_{50}$) against telomerase and several enzymes having nucleic acid binding or modifying activities related to telomerase using standard techniques. The enzymes being screened include Telomerase, DNA Polymerase I, HeLa RNA Polymerase II, T3 RNA Polymerase, MMLV Reverse Transcriptase, Topoisomerase I, Topoisomerase II, Terminal Transferase and Single-Stranded DNA Binding Protein (SSB). The specificity of a compound of the invention for telomerase is determined by comparing the $IC_{50}$ of the compound with respect to telomerase with the $IC_{50}$. values of the compound for each of the enzymes being screened. The compound is determined to have high specificity for telomerase if the $IC_{50}$ for telomerase of the compound is lower than the $IC_{50}$ vaules for each of the enzymes being screened.

c. Cytotoxicity

The XTT assay for cytotoxicity is performed using HeLa cells. The cell lines used in the assay are exposed to a compound of the invention for 72 hours at concentrations ranging from about 1 $\mu$M to about 1,000 $\mu$M. During this period, the optical density (OD) of the samples is determined for light at 540 nanometers (nm). No significant cytotoxic effects are expected to be observed at concentrations less than about 5 $\mu$M. It will be appreciated that other tumor cells lines such as the ovarian tumor cell lines OVCAR-5 and SK-OV-3 can be used to determine cytotoxicity in addition to control cell lines such as normal human BJ cells. Other assays for cytotoxicity such as the MTT assay can be used as well.

Some compounds may induce G2 arrest at concentrations above about 5 $\mu$M (i.e., at 10 $\mu$M-20 $\mu$M concentrations or higher). Preferably, to observe any telomerase inhibiting effects the compounds should be administered at a concentration below the level of cytotoxicity. Nevertheless, since the effectiveness of many cancer chemotherapeutics derives from their cytotoxic effects, it is within the scope of the present invention that the compounds of the present invention be administered at any dose for which chemotherapeutic effects are observed.

2. In vivo Studies

A human tumor xenograft model in which OVCAR-5 tumor cells are grafted into nude mice can be constructed using standard techniques and materials. The mice are divided into two groups. One group is treated intraperitoneally with a compound of the invention. The other group is treated with a control comprising a mixture of either DMSO or ethanol and emulphor (oil) and phosphate buffer solution (PBS). The average tumor mass for mice in each group is determined periodically following the xenograft using standard methods and materials.

In the group treated with a compound of the invention, the average tumor mass is expected to increase following the initial treatment for a period of time, after which time the tumor mass is expected to stabilize and then begin to decline. Tumor masses in the control group are expected to increase throughout the study. Thus, the compounds of the invention are expected to lessen dramatically the rate of tumor growth and ultimately induce reduction in tumor size and elimination of the tumor.

Thus, the present invention provides novel compounds, compositions and methods for inhibiting telomerase activity and treating disease states in which telomerase activity has deleterious effects, especially cancer. The compounds of the invention provide a highly selective and effective treatment for malignant cells that require telomerase activity to remain immortal; yet, without affecting non-malignant cells.

Although certain embodiments and examples have been used to describe the present invention, it will be apparent to those of skill in the art that changes may be made to those described embodiments and examples without departing from the scope or spirit of the invention or the following claims.

What is claimed:

1. A telomerase inhibiting compound having the structure:

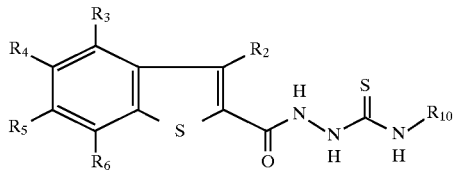

or a pharmaceutically acceptable salt thereof, wherein:
   $R_2$ is selected from the group consisting of hydrogen, chlorine, fluorine, bromine, and iodine;
   $R_3$–$R_6$ are selected independently from the group consisting of hydrogen, amino, nitro, cyano, alkyl, aryl, halogen, alkoxyl, aryloxyl, arylthiocarbamido, alkylthio, aralkoxy, and arylthio; and
   $R_{10}$ is unsubstituted benzyl, unsubstituted allyl, or phenyl substituted optionally with one or more moieties selected independently from the group consisting hydrogen, alkyl, aryl, hydroxyl, alkoxyl, aryloxyl, halogen, cyano, nitro, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, carboxyl, alkyloxycarbonyl, aryloxycarbonyl, sulfo, alkylsulfonyl, arylsulfonyl, alkylthio and arylthio;
   provided that when $R_2$ is chloro, and $R_3$, $R_4$, and $R_6$ are hydrogen, then:
   $R_{10}$ is not phenyl or phenyl substituted at the para position with methoxy or chloro when $R_5$ is methoxy or hydrogen; and
   $R_{10}$ is not para-methylphenyl, unsubstituted benzyl or unsubstituted allyl when $R_5$ is hydrogen.

2. The compound of claim 1, wherein $R_2$ is hydrogen.

3. The compound of claim 2, wherein $R_3$, $R_5$, and $R_6$ are hydrogen, $R_4$ is N-(4-methylphenyl)thiocarbamido and $R_{10}$ is 2,5-dichlorophenyl.

4. The compound of claim 2, wherein $R_3$, $R_4$, and $R_6$ are hydrogen, and $R_5$ is N-[2-(4-methylphenylthio)phenyl]thiocarbamido and $R_{10}$ is 2-(4-methylphenylthio)phenyl.

5. The compound of claim 2, wherein $R_3$, $R_5$, and $R_6$ are hydrogen, $R_4$ is N-(3-methylphenyl)thiocarbamido, and $R_{10}$ is 3,5-bis(trifluoromethyl)phenyl, 2-(4-methylphenylthio)phenyl, or 4-(methylthio)phenyl.

6. The compound of claim 2, wherein $R_3$–$R_6$ are hydrogen and $R_{10}$ is 2,5-dichlorophenyl.

7. The compound of claim 2, wherein $R_3$–$R_5$ are hydrogen, $R_6$ is fluoro, and $R_{10}$ is selected from the group consisting of 2,4,5-trichlorophenyl, 2,3,4,5-tetrachlorophenyl, and 2-(4-methylphenylthio)phenyl.

8. The compound of claim 2, wherein $R_3$ is chloro, $R_4$–$R_6$ are hydrogen, and $R_{10}$ is selected from the group consisting of 2,4,5-trichlorophenyl, 2,3,4,5-tetrachlorophenyl, 2,5-dibromophenyl, 2,3,4-trichlorophenyl, and 2-(4-methylphenylthio)phenyl.

9. The compound of claim 2, wherein $R_3$ is fluoro, $R_4$–$R_6$ are hydrogen, and $R_{10}$ is 4-(4-nitrophenylthio)phenyl.

10. The compound of claim 1, wherein $R_2$ is halogen.

11. The compound of claim 10, wherein $R_2$ is chloro.

12. The compound of claim 10, wherein $R_3$ and $R_4$ are hydrogen.

13. The compound of claim 12, wherein $R_6$ is hydrogen or halogen.

14. The compound of claim 13, wherein $R_5$ is methoxy, $R_6$ is chloro, and $R_{10}$ is 2,4,5-trichlorophenyl or 2,3,4,5-tetrachlorophenyl.

15. The compound of claim 13, wherein $R_6$ is hydrogen.

16. The compound of claim 15, wherein $R_5$ is hydrogen and $R_{10}$ is 2,5-dichlorophenyl or 2,3,4,5-tetrachlorophenyl.

17. The compound of claim 15, wherein $R_5$ is methoxy and $R_{10}$ is 2,4,5-trichlorophenyl, 2,3,4,5-tetrachlorophenyl, or 2,3,4-trichlorophenyl.

18. The compound of claim 15, wherein $R_5$ is methyl and $R_{10}$ is 2,3-dichlorophenyl.

19. The compound of claim 15, wherein $R_5$ is phenyl and $R_{10}$ is selected from the group consisting of 2,4,5-trichlorophenyl, 2,3,4,5-tetrachlorophenyl, 2,3-dichlorophenyl, 2,5-dichlorophenyl, 2,5-dibromophenyl, and 2,4,6-trichlorophenyl.

20. The compound of claim 11, wherein $R_3$ and $R_4$ are chloro, $R_5$ and $R_6$ are hydrogen, and $R_{10}$ is selected from the group consisting of 2,3,4,5-tetrachlorophenyl, 2,3-dichlorophenyl, 2,4-dichlorophenyl, 2,5-dichlorophenyl, 2,3,4-trichlorophenyl, 2,5-dibromophenyl, 3,5-bis(trifluoromethyl)phenyl, 2-(4-methylphenylthio)phenyl, 2-naphthyl, 2,4,5-trichlorophenyl, 2,4,6-trichlorophenyl, and 4-chlorophenyl.

21. A method of treating cancer in a mammal, comprising administering to such mammal a therapeutically effective amount of a compound having the structure shown below, and the pharmaceutically acceptable salts thereof, to inhibit telomerase activity in cancer cells in such mammal such that the telomeres of said cancer cells are reduced in length over successive cell divisions

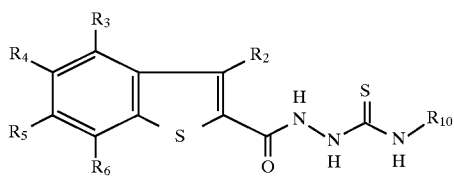

wherein:

R$_2$ is selected from the group consisting of hydrogen, fluorine, bromine, and iodine;

R$_3$–R$_6$ are selected independently from the group consisting of hydrogen, amino, nitro, cyano, alkyl, artl, halogen, alkoxyl, aryoxyl, arylthiocarbamido, alklylthio, aralkoxy, and arylthio; and R$_{10}$ is phenyl substituted optionally with one or more moieties selected independently from the group consisting hydrogen, alkyl, aryl, hydroxyl, alkoxyl, aryloxyl, halogen, cyano, nitro, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, carboxyl, alkyloxycarbonyl, aryloxycarbonyl, sulfo, alkylsulfonyl, arylsulfonyl, alkylthio and arylthio.

22. A composition for treating cancer, comprising a therapeutically effective amount of a compound having the structure shown in claim 21 in a pharmaceutically acceptable carrier.

* * * * *